United States Patent
Kawasaki et al.

(10) Patent No.: US 6,683,186 B2
(45) Date of Patent: Jan. 27, 2004

(54) 2,3-DISUBSTITUTED PYRIDINE DERIVATIVE, PROCESS FOR THE PREPARATION THEREOF, PHARMACEUTICAL COMPOSITION CONTAINING THE SAME, AND INTERMEDIATE THEREFOR

(75) Inventors: Motoji Kawasaki, Ikeda (JP); Tomohiro Nigo, Takarazuka (JP)

(73) Assignee: Dainippon Pharmaceutical Company, Limited, Osaka-fu (JP)

( * ) Notice: Subject to any disclaimer, the term of this patent is extended or adjusted under 35 U.S.C. 154(b) by 0 days.

(21) Appl. No.: 10/383,585

(22) Filed: Mar. 10, 2003

(65) Prior Publication Data

US 2003/0199554 A1 Oct. 23, 2003

Related U.S. Application Data

(62) Division of application No. 09/787,766, filed as application No. PCT/JP99/05385 on Sep. 30, 1999, now Pat. No. 6,555,557.

(30) Foreign Application Priority Data

Oct. 6, 1998 (JP) ............................................ 10-283848

(51) Int. Cl.$^7$ .................... C07D 213/70; C07D 213/69; C07D 401/12
(52) U.S. Cl. ....................................... 546/261; 546/256
(58) Field of Search ................................. 546/256, 261

(56) References Cited

U.S. PATENT DOCUMENTS 4,193,926 A    3/1980    Schmiechen et al. .... 260/326.5

FOREIGN PATENT DOCUMENTS

| EP | 0 303 465 | 2/1989 |
|----|-----------|--------|
| EP | 0 773 024 | 5/1997 |
| HU | P9502568 A | 6/1996 |
| WO | 92/12961 | 8/1992 |
| WO | 93/19749 | 10/1993 |
| WO | 94/12461 | 4/1994 |
| WO | 97/22586 | 6/1997 |
| WO | 98/45268 | 10/1998 |
| WO | 99/02519 | 2/1999 |

OTHER PUBLICATIONS

CA 136:48451, Kawaski et al.
H. Sliwa et al., "Synthesis of New Fundamental Hterocycles IX Heterocycles", vol. 12, No. 4, pp. 493–495, 1979.
D. Cavalla et al., "Phosphodiesterase IV Inhibitors: Structural Diversity and Therapeutic Potential in Asthma", Current Medicinal Chemistry, vol. 2, pp. 561–572, 1995.

Primary Examiner—Patricia L. Morris
(74) Attorney, Agent, or Firm—Wenderoth, Lind & Ponack, L.L.P.

(57) ABSTRACT

A compound of the formula (I)

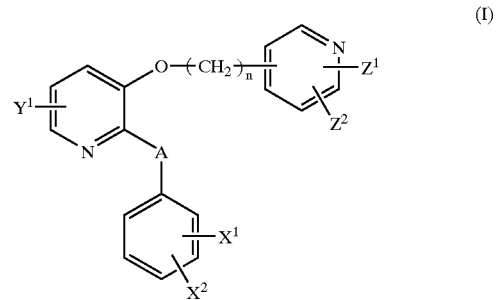

wherein A is O, S, $CHR^1$ or $NR^2$, $R^1$ and $R^2$ are H, lower alkyl, $X^1$ and $X^2$ are H, halogen, nitro, cyano, etc., $Y^1$ is H, lower alkyl, $Z^1$ and $Z^2$ are H, halogen, cyano, hydroxy, lower alkyl, etc., and n is an integer of 2 to 4, a pharmaceutically acceptable salt thereof, a process for preparing the same, a pharmaceutical composition containing the same as an active ingredient, and an intermediate therefor. The compounds (I) of the present invention show a potent PDE IV inhibitory activity as well as an excellent bronchodilating activity, and hence, they are widely useful as a PDE IV inhibitor in the treatment or prophylaxis of allergic inflammatory diseases or organ inflammatory diseases, especially in the treatment or prophylaxis of pulmonary diseases accompanied by airway obstruction such as asthma.

1 Claim, No Drawings

2,3-DISUBSTITUTED PYRIDINE DERIVATIVE, PROCESS FOR THE PREPARATION THEREOF, PHARMACEUTICAL COMPOSITION CONTAINING THE SAME, AND INTERMEDIATE THEREFOR

This application is a divisional application of Ser. No. 09/787,766 filed Mar. 22, 2001, now U.S. Pat. No. 6,555, 557, which is a 371 of International Application No. PCT/JP99/05385 filed Sep. 30, 1999.

TECHNICAL FIELD

The present invention relates to a novel 2,3-disubstituted pyridine derivative exhibiting a phosphodiesterase IV (hereinafter, referred to as PDE IV) inhibitory activity being useful as a medicament, a process for the preparation thereof, a pharmaceutical composition containing the same, and an intermediate therefor.

BACKGROUND ART

Hitherto, theophylline or various chemical mediator antagonists have been used as an agent for treatment of asthma, but these agents have defects, for example, they cannot exhibit a sufficient inhibitory effect on bronchoconstriction or a sufficient effect on airway inflammatory and they cannot show a sufficient selectivity from their side effects on the cardiovascular system. Steroids also have been used as an agent for treatment of asthma, and their effects on the airway inflammation are potent but their inhibitory effects on bronchoconstriction is weak, and in addition, serious side effects of steroids have also been predicted. Therefore, it has been desired to develop a novel agent exhibiting an inhibitory effect on bronchoconstriction as well as an effect on the airway inflammation.

PDE IV widely distributes onto the bronchial smooth muscle and inflammatory cells including eosinophil, and it is an enzyme catalyzing the destruction of cyclic AMP (hereinafter, occasionally referred to as cAMP). It has widely been known that by inhibiting PDE IV, the constriction of the bronchial smooth muscle is prevented, and the activation of inflammatory cells is prevented (Current Medicinal Chemistry, vol. 2, p. 561–572 (1995)).

The compounds of the following formulae, for example, Rolipram (U.S. Pat. No. 4,193,926), RP-73401 (WO 92 12961), SB-207499 (WO 93 19749), are exemplified as a representative compound having a PDE IV inhibitory activity.

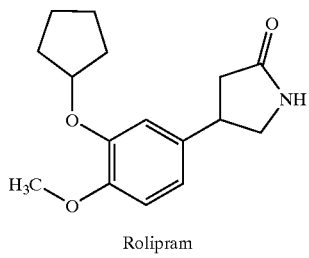

Rolipram

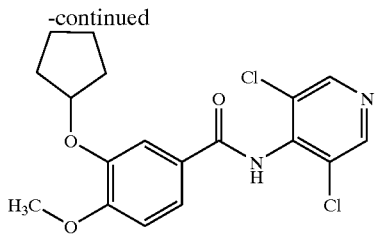

RP-73401

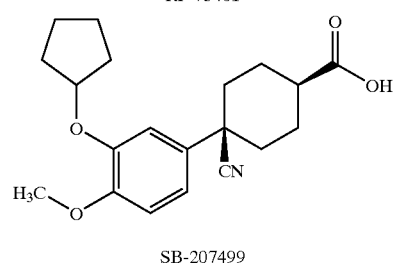

SB-207499

In addition, EP 773024 discloses that an N-substituted nicotinamide compound of the following formula (A) exhibits a PDE IV inhibitory activity.

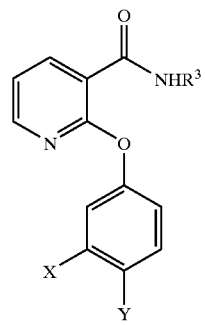

(A)

wherein $R^3$ is 1-piperidyl, phenyl, benzyl, etc., Y is hydrogen, fluoro or chloro, and X is hydrogen, fluoro, chloro, methoxy, trifluoromethyl, cyano, carboxy, methylcarbamoyl, dimethylcarbamoyl or a carbo ($C_1$–$C_4$) alkoxy.

In addition, WO 9845268 discloses that a nictoninamide compound of the following formula (B) exhibits a PDE IV inhibitory activity.

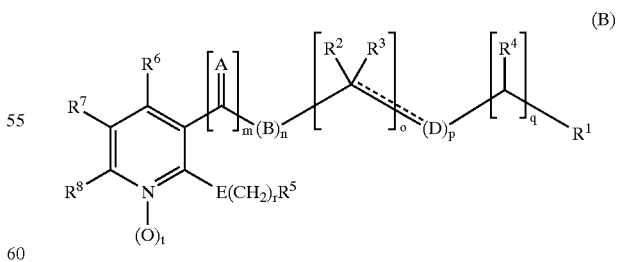

(B)

wherein m is 0 or 1, n is 0 or 1, o is 0, 1, 2, 3, or 4, p is 0 or 1, q is 0, 1, 2, or 3, r is 0, 1, 2, 3, or 4, t is 0 or 1, A is an oxygen atom, >NH, etc., B is an oxygen atom or NH, D is an oxygen atom or $NR^9$, E is $CH_2$, an oxygen atom, NH or $S(O)_a$, $R^1$ is a hydrogen atom, a ($C_1$–$C_6$)alkyl group, a ($C_3$–$C_7$)heterocyclic group, etc., $R^2$, $R^3$ and $R^4$ are a hydrogen atom, a hydroxy group, etc., $R^5$ is a $(C_3-C_7)$heterocycle, $R^6$, $R^7$ and $R^8$ are a hydrogen atom, a $(C_1-C_6)$alkyl group, etc.

However, conventional PDE IV inhibitors cannot show a sufficient bronchodilating activity, and under such circumstances, it has been desired to develop a novel PDE IV inhibitor exhibiting more potent bronchodilating activity as well as effects on the airway inflammation.

On the other hand, a compound of the above formula (A) or (B) wherein the 3-substituent of the pyridine ring is a pyridylalkyleneoxy group has never been known.

An object of the present invention is to provide a novel 2,3-disubstituted pyridine derivative and a pharmaceutically acceptable salt thereof, which show an excellent PDE IV inhibitory activity.

DISCLOSURE OF INVENTION

The present invention relates to a 2,3-disubstituted pyridine derivative of the following formula (I) or a pharmaceutically acceptable salt thereof, a phosphodiesterase IV inhibitor containing said compound as an active ingredient, and a pharmaceutical composition containing the same.

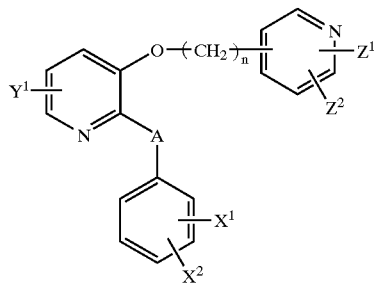

(I)

wherein A is an oxygen atom, a sulfur atom, $CHR^1$ or $NR^2$, $R^1$ and $R^2$ are a hydrogen atom or a lower alkyl group;

$X^1$ and $X^2$ are the same or different and each a hydrogen atom, a halogen atom, a nitro group, a cyano group, a hydroxy group, a lower alkyl group, a hydroxy-substituted lower alkyl group, a halogeno-lower alkyl group, a lower alkoxy group, a cyclo-lower alkoxy group, a hydroxy-substituted lower alkoxy group, a halogeno-lower alkoxy group, a lower alkoxy-substituted lower alkoxy group, a carboxy-substituted lower alkoxy group, a lower alkoxycarbonyl-substituted lower alkoxy group, a carboxyl group, a lower alkoxycarbonyl group, a mono- or di-lower alkylaminocarbonyl group, a lower acyl group, a lower acyloxy group, an amino group, a lower acylamino group, a carbamoyl group, a 5-tetrazolyl group, or a group which can be converted into a hydroxy group in vivo;

$Y^1$ is a hydrogen atom or a lower alkyl group;

$Z^1$ and $Z^2$ are the same or different and each a hydrogen atom, a halogen atom, a cyano group, a hydroxy group, a lower alkyl group, a hydroxy-substituted lower alkyl group, a halogeno-lower alkyl group, a lower alkoxy group, a cyclo-lower alkoxy group, a hydroxy-substituted lower alkoxy group, a halogeno-lower alkoxy group, a lower alkoxy-substituted lower alkoxy group, a carboxy-substituted lower alkoxy group, a lower alkoxycarbonyl-substituted lower alkoxy group, a carboxyl group, a lower alkoxycarbonyl group, a mono- or di-lower alkylaminocarbonyl group, a lower acyloxy group, an amino group, a mono- or di-lower alkylamino group, a lower acylamino group, a lower alkoxycarbonylamino group, a lower alkylsulfonylamino group, a carbamoyl group, a 5-tetrazolyl group, or a group which can be convereted into a hydroxy group in vivo; and n is an integer of 2 to 4.

The pharmaceutically acceptable salt includes a pharmaceutically acceptable acid addition salt, an alkali metal salt, an alkaline earth metal salt or a salt with an organic base. For example, the acid addition salt includes a salt with an inorganic acid such as hydrochloride, hydrobromide, hydroiodide, sulfate, phosphate, etc., or a salt with an organic acid such as oxalate, maleate, fumarate, malonate, lactate, malate, citrate, tartrate, benzoate, methanesulfonate, p-toluenesulfonate, gluconate, etc. The alkali metal salt includes, for example, a salt with an inorganic alkali metal such as sodium salt, potassium salt, and the alkaline earth metal salt includes, for example, calcium salt, magnesium salt. The salt with an organic base includes, for example, a salt with ammonia, methylamine, triethylamine, tributylamine, diisopropylethylamine, N-methylmorpholine, dicyclo-hexylamine.

The present compound of the formula (I) and a pharmaceutically acceptable salt thereof may exist in the form of a hydrate and/or a solvate, and the present invention also includes these hydrates and solvates as well.

The present compounds of the formula (I) may optionally have one or more asymmetric carbon atoms, and the present invention also includes these stereoisomers and a mixture thereof.

When $Z^1$ or $Z^2$ is a hydroxy group and these groups attach to the 2-position or the 4-position of the pyridine ring, the present compounds of the formula (I) may have a keto-enol tautomer, and the present invention also includes these tautomers, and a mixture thereof.

In the compound (I), the group being able to be converted into a hydroxy group in vivo means a group which can be enzymatically or non-enzymatically destructed to a hydroxy group in vivo, for example, one wherein a hydroxy group is acylated, carbonated or carbamated by an acetyl group, a propionyl group, a benzoyl group, an ethoxycarbonyl group, a carbamoyl group, an amino acid residue, etc. Hereinafter, compounds having such groups may occasionally be referred as a prodrug.

The present invention also relates to an intermediate for preparing a 2,3-disubstituted pyridine derivative of the above formula (I), i.e., a pyridine derivative of the following formula (II):

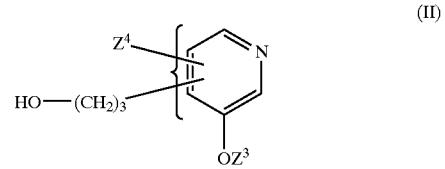

(II)

wherein $Z^3$ is a hydrogen atom, a lower alkyl group, a cyclo-lower alkyl group, a lower alkoxy-substituted lower alkyl group, a lower acyl group, a benzyl group, a benzoyl group, or a mono- or di-lower alkoxy-substituted benzoyl group, $Z^4$ is a hydrogen atom, a halogen atom, a cyano group, a lower alkoxycarbonyl group, a lower acyloxy group, a lower alkoxy group, a lower alkoxy-substituted lower alkoxy group, an amino group, a lower alkoxycarbonylamino group, or a lower alkylsulfonylamino group.

The terms used in the specification are explained below.

The "lower alkyl group" and the "lower alkyl moiety" include a straight chain or branched chain alkyl group having 1 to 6 carbon atoms, for example, methyl, ethyl, propyl, isopropyl, butyl, isobutyl, sec-butyl, tert-butyl, hexyl, etc.

The "halogeno-lower alkyl group" and the "halogeno-lower alkyl moiety" include a straight chain or branched chain alkyl group having 1 to 6 carbon atoms, which is substituted by a halogen atom, for example, trifluoromethyl group.

The "cyclo-lower alkyl group" and the "cyclo-lower alkyl moiety" include a cyclic alkyl group having 3 to 6 carbon atoms, for example, cyclopentyl and cyclohexyl.

The "lower acyl group" and the "lower acyl moiety" include a straight chain or branched chain alkanoyl group having 1 to 5 carbon atoms, for example, formyl, acetyl, propionyl, butyryl, isobutyryl, valeryl, and pivaloyl.

The "halogen atom" is fluorine atom, chlorine atom, bromine atom, and iodine atom.

The "lower alkoxy group" and the "lower alkoxy moiety" include a straight chain or branched chain alkoxy group having 1 to 6 carbon atoms, for example, methoxy, ethoxy, propoxy, isopropoxy, butoxy, isobutoxy, sec-butoxy, tert-butoxy, and hexyloxy.

The "cyclo-lower alkoxy group" and the "cyclo-lower alkoxy moiety" include a cyclic alkoxy group having 3 to 6 carbon atoms, for example, cyclopentyloxy and cyclohexyloxy.

The "lower alkenyl group" and the "lower alkenyl moiety" include a straight chain or branched chain alkenyl group having 2 to 6 carbon atoms, for example, allyl, 2-butenyl, and 3-methyl-2-butenyl.

Among the present compounds (I) of the present invention, preferable one is a compound of the formula (I) wherein A is an oxygen atom, a sulfur atom, $CH_2$ or NH, $Z^1$ and $Z^2$ are the same or different and each a hydrogen atom, a halogen atom, a hydroxy group, a lower alkoxy group, a cyclo-lower alkoxy group, a hydroxy-substituted lower alkoxy group, a halogeno-lower alkoxy group, a carboxyl-substituted lower alkoxy group, a lower alkoxycarbonyl-substituted lower alkoxy group, a mono- or di-lower alkylaminocarbonyl group, a lower acyloxy group, an amino group, a mono- or di-lower alkylamino group, a lower acylamino group, a lower alkoxycarbonylamino group, a lower alkylsulfonylamino group, a carbamoyl group, or a group which can be converted into a hydroxy group in vivo, or a pharmaceutically acceptable salt thereof.

More preferable compounds are compounds of the formula (Ia) or a pharmaceutically acceptable salt thereof.

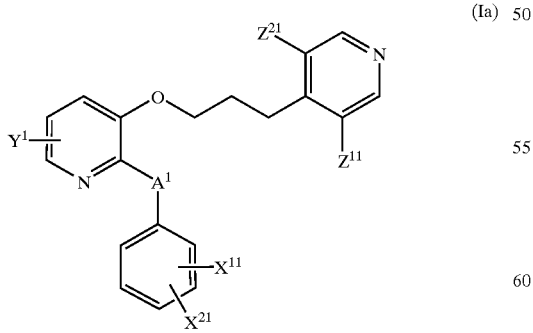

(Ia)

wherein $A^1$ is an oxygen atom, a sulfur atom, $CH_2$ or NH;
$X^{11}$ is a hydrogen atom, a halogen atom, a nitro group, a cyano group, a hydroxy group, a lower alkyl group, a hydroxy-substituted lower alkyl group, a halogeno-lower alkyl group, a lower alkoxy group, a hydroxy-substituted lower alkoxy group, a halogeno-lower alkoxy group, a lower alkoxycarbonyl group, a mono- or di-lower alkylaminocarbonyl group, or a lower acyl group;

$X^{21}$ is a hydrogen atom, a halogen atom, a lower alkyl group, a lower alkoxy group, a hydroxy-substituted lower alkoxy group, a halogeno-lower alkoxy group;

$Y^1$ is a hydrogen atom or a lower alkyl group;

$Z^{11}$ and $Z^{21}$ are the same or different and each a hydrogen atom, a halogen atom, a hydroxy group, a lower alkoxy group, a cyclo-lower alkoxy group, a hydroxy-substituted lower alkoxy group, a halogeno-lower alkoxy group, a lower alkoxy-substituted lower alkoxy group, a carboxy-substituted lower alkoxy group, a lower alkoxycarbonyl-substituted lower alkoxy group, a mono- or di-lower alkylaminocarbonyl group, a lower acyloxy group, an amino group, a mono- or di-lower alkylamino group, a lower acylamino group, a lower alkoxycarbonyl-amino group, a lower alkylsulfonylamino group, a carbamoyl group, or a group which can be converted into a hydroxy group in vivo.

Especially preferable compounds are the following compounds or a pharmaceutically acceptable salt thereof.

2-phenoxy-3-[3-(pyridin-4-yl)propoxy]pyridine;

2-(3-bromophenoxy)-3-[3-(pyridin-4-yl)propoxy]pyridine;

2-(3-fluorophenoxy)-3-[3-(pyridin-4-yl)propoxy]pyridine;

2-(3-fluorophenoxy)-3-[3-(3-hydroxypyridin-4-yl)propoxy]-pyridine;

2-(3-chlorophenoxy)-3-[3-(3-hydroxypyridin-4-yl)propoxy]-pyridine;

2-(3-bromophenoxy)-3-[3-(3-hydroxypyridin-4-yl)propoxy]-pyridine;

2-(3-chlorophenoxy)-3-[3-(3-aminopyridin-4-yl)propoxy]pyridine;

2-phenoxy-3-[3-(3-hydroxypyridin-4-yl)propoxy]pyridine;

2-phenoxy-3-[3-(3-acetoxypyridin-4-yl)propoxy]pyridine;

2-(3-chlorophenoxy)-3-[3-(3-acetoxypyridin-4-yl)propoxy]-pyridine;

2-(3-chlorophenoxy)-3-[3-(3-chloro-5-hydroxypyridin-4-yl)-propoxy]pyridine;

2-(3-chlorophenoxy)-3-[3-(3-hydroxypyridin-5-yl)propoxy]-pyridine;

2-(3-chlorophenoxy)-3-[3-(3-amino-5-hydroxypyridin-4-yl)-propoxy]pyridine;

2-(3-chlorophenoxy)-3-[3-(3-methylsulfonylaminopyridin-4-yl)-propoxy]pyridine; and 2-(3-bromophenylthio)-3-[3-(pyridin-4-yl)propoxy]pyridine.

The representative compounds (I) of the present invention are the compounds as listed in the following Table 1 or a pharmaceutically acceptable salt thereof, in addition to the compounds of Examples as disclosed hereinbelow.

TABLE 1

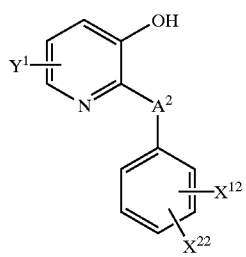

| A | n | Attaching Position | $X^1$ | $X^2$ | $Y^1$ | $Z^1$ | $Z^2$ |
|---|---|---|---|---|---|---|---|
| $CH_2$ | 3 | 4 | 3-Br | H | H | H | H |
| O | 3 | 4 | 3-$CONH_2$ | H | H | H | H |
| O | 3 | 4 | 3-$CH_2OH$ | H | H | H | H |
| O | 3 | 4 | 3-$CONMe_2$ | H | H | H | H |
| O | 3 | 4 | 3-$NH_2$ | H | H | H | H |
| O | 3 | 4 | 3-NHAc | H | H | H | H |
| O | 3 | 3 | H | H | H | 2-OH | H |
| O | 3 | 3 | H | H | H | 6-OH | H |
| NH | 3 | 4 | H | H | H | H | H |
| O | 3 | 4 | 3-Br | H | H | 3-OH | 2-$CH_2OH$ |
| S | 3 | 4 | 3-Cl | H | H | 3-OH | H |
| O | 3 | 4 | 3-Cl | 2-OMe | H | 3-OH | H |
| O | 3 | 4 | 3-Cl | H | H | 3-$OCONMe_2$ | H |
| O | 3 | 4 | 3-Br | H | H | 3-OAc | H |
| O | 3 | 4 | 3-Cl | H | H | 3-pivaloyloxy | H |
| O | 3 | 4 | 3-$OCF_3$ | H | H | 3-OH | H |
| O | 3 | 4 | 3-Cl | H | H | 3-$CH_2OH$ | H |
| O | 3 | 4 | 3-Cl | H | H | 3-NHAc | H |
| O | 3 | 4 | 3-Cl | H | H | 3-$CONH_2$ | H |
| O | 3 | 4 | 3-Cl | H | 6-Me | 3-OH | H |
| O | 3 | 4 | 3-Cl | H | 4-Me | 3-OH | H |
| O | 3 | 4 | 3-Cl | H | H | 2-OH | H |
| O | 2 | 4 | 3-Cl | H | H | 3-OH | H |
| O | 3 | 4 | 3-Cl | H | H | 3-(5-tetrazolyl) | H |

Note: Attaching position means the position at which the alkylene group is bonded to the pyridine ring. In Table 1, the following abbreviations are used in order to simplify the description. Me: methyl group, Ac: acetyl group.

The compounds (I) of the present invention may be prepared, for example, by the following processes (a) and (b), as explained below.

Process (a):

The compound of the formula (I) wherein A is an oxygen atom, a sulfur atom or $CHR^1$ may be prepared, if necessary, by protecting by a conventional method a compound of the formula (III):

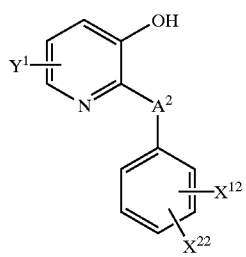

(III)

wherein $A^2$ is an oxygen atom, a sulfur atom or $CHR^1$, $X^{12}$ and $X^{22}$ are the same or different and each a hydrogen atom, a halogen atom, a nitro group, a cyano group, a lower alkyl group, a halogeno-lower alkyl group, a lower alkoxy group, a cyclo-lower alkoxy group, a halogeno-lower alkoxy group, a lower alkoxy-substituted lower alkoxy group, a lower alkoxycarbonyl group, a lower acyl group or a lower acyloxy group, and $R^1$ and $Y^1$ are as defined above, and a compound of the formula (IV):

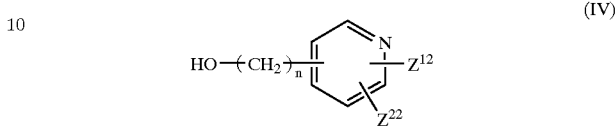

(IV)

wherein $Z^{12}$ and $Z^{22}$ are the same or different and each a hydrogen atom, a halogen atom, a cyano group, a hydroxy group, a lower alkyl group, a lower alkoxy group, a cyclo-lower alkoxy group, a lower alkoxy-substituted lower alkoxy group, a lower alkoxycarbonyl group, a lower acyloxy group, a benzyloxy group, a benzoyloxy group, a mono- or di-lower alkoxy-substituted benzoyl group, a mono- or di-lower alkoxy-substituted benzoyloxy group, an amino group, a lower alkoxycarbonyl-amino group or a lower alkylsulfonylamino group, and n is as defined above, followed by condensing these compounds in the presence of a triphenylphosphine and a dialkyl azodicarboxylate in a suitable solvent, then, if necessary, by removing the protecting groups from the resultant, and further converting the substituents $X^{12}$, $X^{22}$, $Z^{12}$, $Z^{22}$ to other substituents by a conventional method, if required.

The dialkyl azodicarboxylate includes, for example, dimethyl azodicarboxylate, diethyl azodicarboxylate, diisopropyl azodicarboxylate, dibenzyl azodicarboxylate, etc. In addition, a trialkylphosphine such as tri-n-butylphosphine, etc. may be used instead of triphenyl-phosphine. The reaction is preferably carried out at a temperature of from −50° C. to 120° C., more preferably at a temperature of from 0° C. to 80° C. The solvent may be tetrahydrofuran, toluene, xylene, dichloromethane, etc.

The compound of the formula (IV) may include a compound of the above formula (II), i.e., a compound of the (IV) wherein one of $Z^{12}$ and $Z^{22}$ is bonded to the 3-position of the pyridine ring as $OZ^3$, and the other is bonded to the 4- or 5-position of the pyridine ring as $Z^4$, and a hydroxyalkylene group wherein n is 3 is bonded to the 4- or 5-position of the pyridine ring to which the above $Z^4$ is not bonded.

Process (b):

The compound of the formula (I) wherein A is an oxygen atom, a sulfur atom or $NR^2$ may be prepared by reacting a compound of the formula (V):

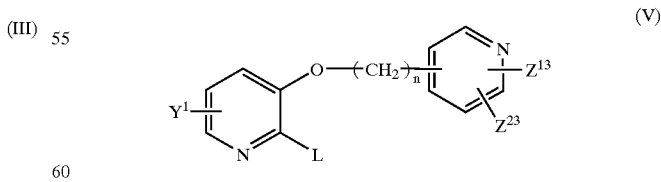

(V)

wherein L is a halogen atom or a nitro group, $Z^{13}$ and $Z^{23}$ are the same or different and each a hydrogen atom, a halogen atom, a cyano group, a lower alkyl group, a lower alkoxy group, a cyclo-lower alkoxy group, a lower alkoxy-substituted lower alkoxy group, or a lower alkoxycarbonyl group, and $y^1$ and n are as defined above, with a compound of the formula (VI):

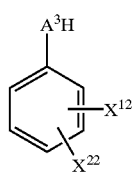
(VI)

wherein $A^3$ is an oxygen atom, a sulfur atom or $NR^2$, and $R^2$, $X^{12}$ and $X^{22}$ are as defined above,
in the presence of a base and a copper catalyst in a suitable solvent, and if necessary, by removing the protecting groups from the resulting compound, and then further followed by converting the substituents $X^{12}$, $X^{22}$, $Z^{13}$, $Z^{23}$ to other substituents by a conventional method, if required. The base is preferably an alkali metal hydride, an alkali metal carbonate, etc. The copper catalyst may preferably be cuprous iodide, cuprous bromide, cuprous chloride, copper powder, cuprous oxide, cupric bromide, etc. The reaction is carried out at a temperature of from 80° C. to 220° C., preferably at a temperature of from 100° C. to 180° C. The solvent may preferably be dimethylformamide, dimethylimidazolidinone, dimethylsulfoxide, dimethylacetamide, pyridine, toluene, xylene, etc.

Processes for preparing the starting compounds for Processes (a) and (b), i.e., the compounds of the formulae (II) to (VI), are explained below.

Process for Preparing the Compound of the Formula (III):

The compound of the formula (III) which is a starting compound for Process (a) wherein A is an oxygen atom, i.e., the compound of the formula (1-4), may be prepared according to the following Scheme 1. Namely, a compound of the formula (1-1) and a compound of the formula (1-2) are reacted in the presence of a base and a copper catalyst in a suitable solvent, and the resulting compound of the formula (1-3) is deprotected to give a compound of the formula (1-4).

Scheme 1

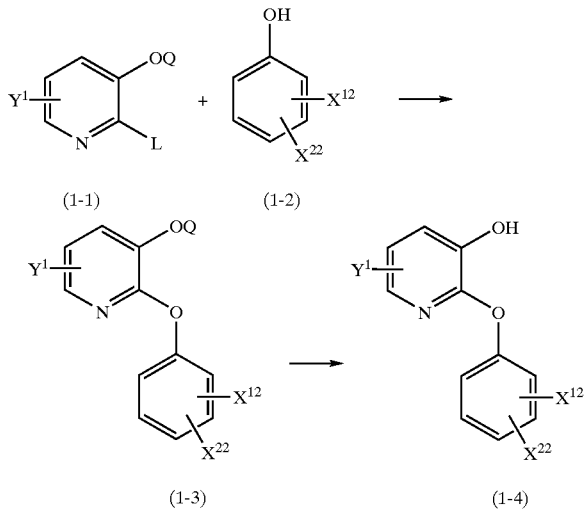

wherein Q is a lower alkyl group, a cyclo-lower alkyl group, a lower alkoxy-substituted lower alkyl group, a lower alkenyl group, a benzyl group, or a tetrahydropyranyl group, and L, $X^{12}$, $X^{22}$ and $Y^1$ are as defined above.

The compound of the formula (1-1) or (1-2) may be commercially available ones or may be prepared by a conventional method. The base may be an alkali metal hydride, an alkali metal carbonate, etc. The copper catalyst may preferably be cuprous iodide, cuprous bromide, cuprous chloride, copper powder, cuprous oxide, cupric bromide, etc. The reaction is carried out at a temperature of from 80° C. to 220° C., preferably at a temperature of from 100° C. to 180° C. The solvent may be dimethylformamide, dimethylimidazolidinone, dimethylsulfoxide, dimethylacetamide, pyridine, toluene, xylene, etc.

The starting compound for Process (a), a compound of the formula (III) wherein A is a sulfur atom, i.e., a compound of the formula (2-3) may be prepared according to the following Scheme 2. Namely, a compound of the formula (2-1) and a compound of the formula (2-2) are reacted in a suitable solvent to give a compound of the formula (2-3).

Scheme 2

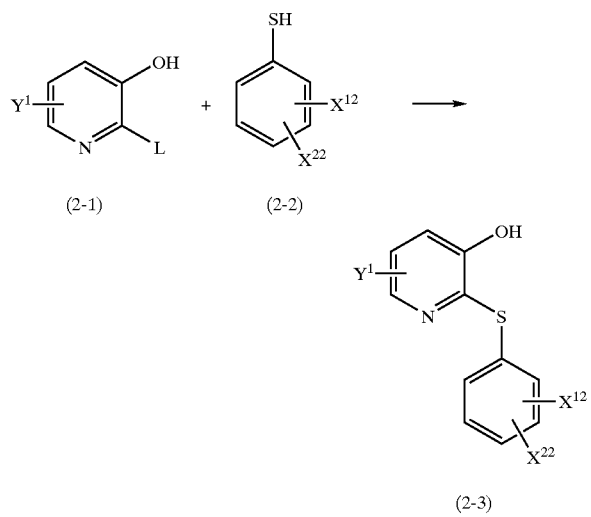

wherein L, $X^{12}$, $X^{22}$ and $Y^1$ are as defined above.

The compound of the formula (2-1) or (2-2) may be commercially available ones or may be prepared by a conventional method. The reaction is carried out at a temperature of from 0° C. to 200° C., preferably at a temperature of from 50° C. to 130° C. The solvent may be dimethylformamide, dimethylimidazolidinone, dimethylsulfoxide, dimethylacetamide, toluene, xylene, tetrahydrofuran, etc.

The starting compound for Process (a), a compound of the formula (III) wherein A is $CHR^1$, i.e., a compound of the formula (3-6) or (3-8) may be prepared according to the following Scheme 3. Namely, a compound of the formula (3-1) is converted to a lithium salt compound of the formula (3-1a), which is further reacted with a compound of the formula (3-2) to give a compound of the formula (3-3). When $R^1$ is a hydrogen atom, a compound of the formula (3-3) is oxidized to give a compound of the formula (3-4), which is further subjected to reduction to give a compound of the formula (3-5). The compound (3-5) is further deprotected to give a compound of the formula (3-6). When $R^1$ is a lower alkyl group, the compound (3-3) is subjected to reduction to give a compound of the formula (3-7), which is further deprotected to give a compound of the formula (3-8).

Scheme 3

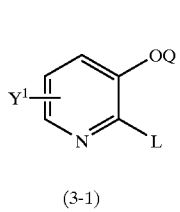 (3-1)

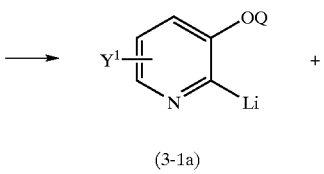 (3-1a) +

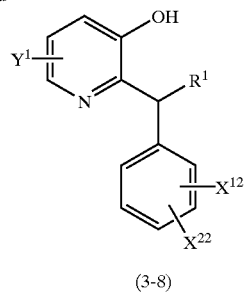 (3-8)

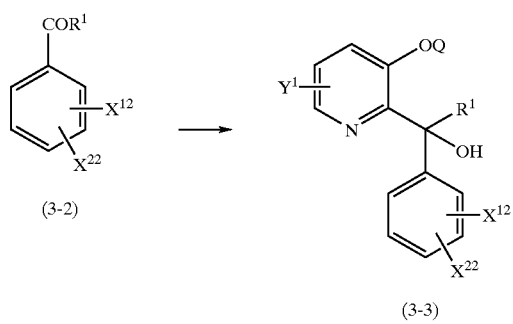 (3-2), (3-3)

In case that $R^1$ is a hydrogen atom:

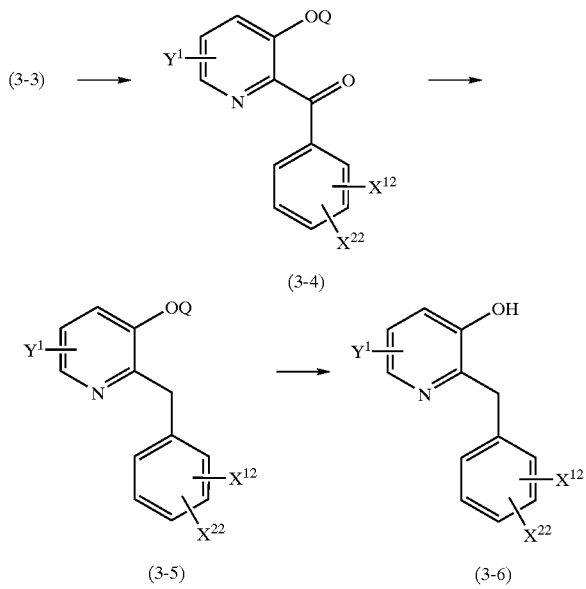 (3-3) → (3-4) → (3-5) (3-6)

In case that $R^1$ is a lower alkyl group:

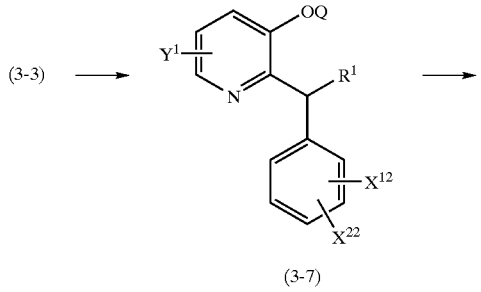 (3-3) → (3-7)

wherein $L^1$ is a bromine atom or a iodine atom, and $R^1$, Q, $X^{12}$, $X^{22}$ and $Y^1$ are as defined above.

The compound of the formula (3-1) or (3-2) may be commercially available ones or may be prepared by a conventional method. The compound of the formula (3-1) can be converted to a corresponding lithium salt thereof by reacting with a base such as n-butyl lithium in a suitable solvent. The reaction is preferably carried out at a temperature of from −150° C. to 100° C., preferably at a temperature of from −80° C. to 0° C. The solvent may be toluene, xylene, tetrahydrofuran, diethyl ether, dioxane, etc.

A compound of the formula (3-2) is added to a reaction solution containing the compound of the formula (3-1a) thus obtained and reacted. The reaction is carried out at a temperature of from −150° C. to 100° C., preferably at a temperature of −80° C. to 0° C.

The compound of the formula (3-4) is obtained by reacting a compound of the formula (3-3) wherein $R^1$ is a hydrogen atom in the presence of an oxidizing agent such as activated manganese dioxide, etc. in a suitable solvent. The reaction is carried out at a temperature of from −20° C. to 120° C., preferably at a temperature of from 0° C. to 100° C. The solvent may be toluene, tetrahydrofuran, dioxane, methylene chloride, hexane, etc.

The reduction of the compound of the formula (3-4) is carried out in the presence of hydrazine and a base in a suitable solvent. The base may be an alkali metal hydroxide such as sodium hydroxide, potassium hydroxide, etc., and the solvent may be ethylene glycol, diethylene glycol, etc. The reaction is carried out at a temperature of from 0° C. to 220° C., preferably at a temperature of from 100° C. to 200° C.

The compound of the formula (3-7) is obtained by subjecting a compound of the formula (3-3) wherein $R^1$ is a lower alkyl group to catalytic reduction in the presence of palladium carbon, and if necessary, in the presence of an acid catalyst such as hydrochloric acid, acetic acid, perchloric acid, etc. in a suitable solvent under hydrogen atmosphere. The reaction is carried out at a temperature of from −40° C. to 110° C., preferably at a temperature of from 0° C. to 70° C. The solvent may be methanol, ethanol, ethyl acetate, toluene, xylene, tetrahydro-furan, dioxane, etc.

The removal of a protecting group from the compound (3-5) and the compound (3-7) is carried out in the presence of a suitable acid such as hydrochloric acid, hydrobromic acid, sulfuric acid, camphor-sulfonic acid, etc. in a suitable solvent such as water, methanol, ethanol, isopropanol, acetic acid, etc. The reaction is carried out at a temperature of from −50° C. to 100° C., preferably at a temperature of from 20° C. to 70° C.

Process for Preparing a Compound of the Formula (II) or the Formula (IV):

The starting compound for Process (a), i.e. the compound of the formula (IV) may be commercially available one or may be prepared according to the following Scheme 4. Besides, the compound of the formula (II) which is within the scope of the compound of the formula (IV), i.e., the compound of the formula (IV) wherein one of $Z^2$ and $Z^{22}$ is bonded to the 3-position of the pyridine ring as $OZ^3$, and the other is bonded to the 4- or 5-position of the pyridine ring as $Z^4$, and a hydroxyalkylene group wherein n is 3 is bonded to the 4- or 5-position of the pyridine ring to which said $Z^4$ is not bonded may be prepared similarly.

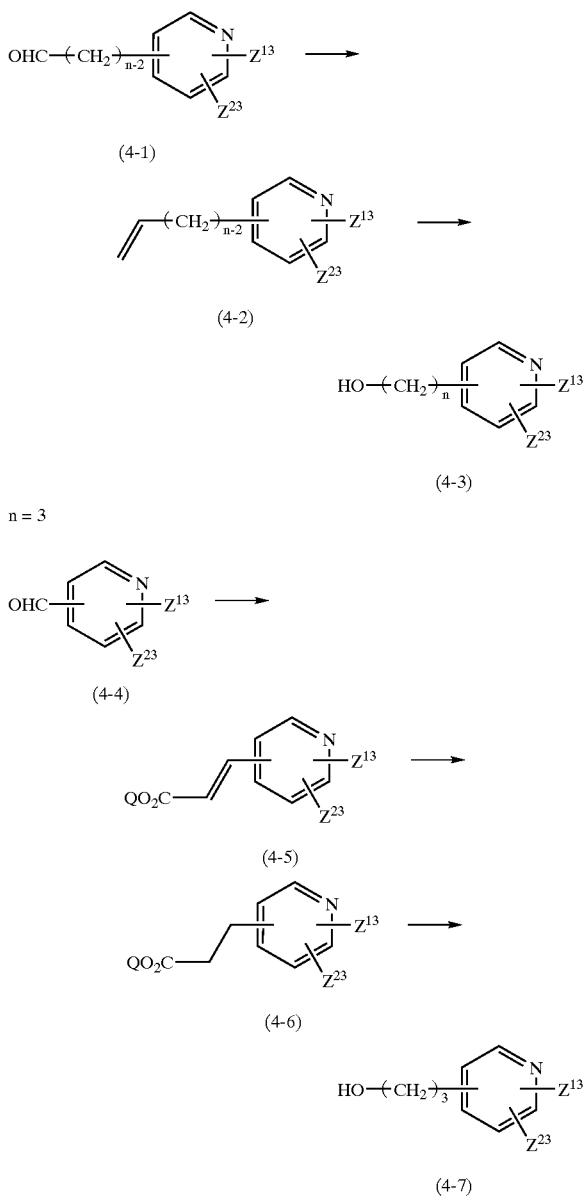

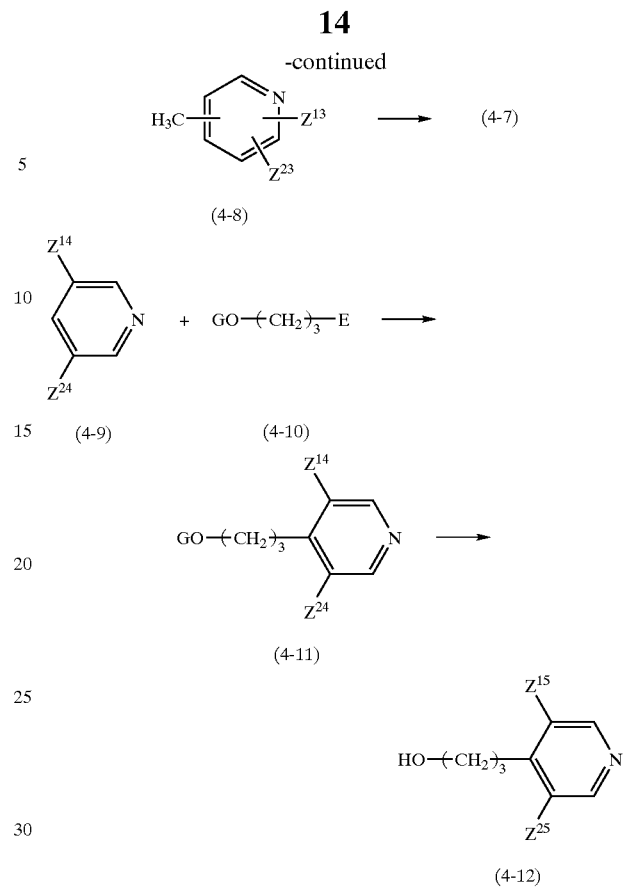

wherein E is a bromine atom or a iodine atom, G is a lower alkyl group, a lower alkoxy-substituted lower alkyl group, an allyl group, a benzyl group or a tetrahydropyranyl group, $Z^{14}$, $Z^{24}$ are a halogen atom, $Z^{15}$, $Z^{25}$ are the same or different and each a halogen atom, a cyano group, a lower alkoxy group, a cyclo-lower alkoxy group, a lower alkoxy-carbonyl group, or a benzyloxy group, and $Z^{13}$, $Z^{23}$ and Q are as defined above.

Among the starting compounds (IV) for Process (a), the compound of the formula (IV) wherein n is 2 or 4 is obtained by reacting a compound of the formula (4-1) with trimethylsilylmethyl magnesium chloride in a suitable solvent, converting the resulting product into a compound of the formula (4-2) by placing it under acidic conditions, further by subjecting the compound (4-2) to hydroboronation reaction, and to subsequently oxidation and hydrolysis to give a compound of the formula (4-3), and if necessary, followed by converting $Z^{13}$ and $Z^{23}$ by a conventional method.

The compound of the formula (4-1) may be commercially available one or may be prepared by a conventional method. The reaction of the compound (4-1) with trimethylsilylmethyl magnesium chloride is preferably carried out at a temperature of from −150° C. to 100° C., preferably at a temperature of from −70° C. to 0° C. The solvent may be toluene, xylene, tetrahydrofuran, diethyl ether, dioxane, etc.

The compound (4-2) thus obtained is subjected to hydroboronation in the presence of a hydroboronating agent such as a complex of borane-pyridine, a complex of borane-tetrahydrofuran, or 6-borabicyclo[3.3.1]nonane, etc. in a suitable solvent, and then further subjected to oxidation and a subsequent hydrolysis under basic conditions. The hydroboronation reaction is carried out at a temperature of from −150° C. to 100° C., preferably at a temperature of from −70° C. to 50° C. The solvent may be tetrahydrofuran, diethyl ether, dioxane, etc. The oxidation reaction and the subsequent hydrolysis are carried out by adding an aqueous solution of an alkali metal hydroxide such as sodium hydroxide, potassium hydroxide, etc. to the reaction solution of hydroboronation, and then by using an aqueous hydrogen peroxide solution. The reaction is carried out at a temperature of from −100° C. to 100° C., preferably at a temperature of from −70° C. to 50° C.

Among the starting compounds (IV) for Process (a), the compound of the formula (IV) wherein n is 3 is prepared by reacting a compound (4-4) with an alkali metal salt of a trialkylphosphonoacetate in a suitable solvent to give the compound (4-5), which is further subjected to catalytic hydrogenation, and further subjecting the resulting compound (4-6) to hydride reduction to give the compound (4-7), and if necessary, followed by converting $Z^{13}$, $Z^{23}$ by a conventional method.

The compound (4-4) may be commercially available one or may be prepared by a conventional method. The reaction of the compound (4-4) is carried out by reacting an alkali metal salt of a trialkylphosphonoacetate, which is obtained by reacting a trialkylphosphonoacetate such as trimethylphosphonoacetate, triethyl-phosphonoacetate, etc. with an alkali metal hydride such as sodium hydride, potassium hydride, etc. in a suitable solvent. The reaction is carried out at a temperature of from −50° C. to 100° C., preferably at a temperature of from −20° C. to 70° C. The solvent may be toluene, xylene, tetrahydrofuran, diethyl ether, dioxane, etc.

The compound (4-5) thus obtained may be converted into a compound of the formula (4-6) by catalytic reduction in the presence of a palladium carbon under hydrogen atmosphere. The reaction is carried out at a temperature of from −40° C. to 110° C., preferably at a temperature of from 0° C. to 70° C. The solvent may be methanol, ethanol, ethyl acetate, toluene, xylene, tetrahydrofuran, dioxane, etc.

Further, the compound (4-6) is subjected to reduction by using a reagent such as lithium aluminum hydride, diisobutyl aluminum hydride, etc., in a suitable solvent. The reaction is carried out at a temperature of from −50° C. to 100° C., preferably at a temperature of from 0° C. to 70° C. The solvent may be toluene, xylene, diethyl ether, tetrahydrofuran, dioxane, etc.

Among the starting compounds (IV) for Process (a), the compound of the formula (IV) wherein n is 3 may also be prepared by reacting a compound of the formula (4-8) with ethylene oxide in the presence of a base to give a compound of the formula (4-7), and if necessary, followed by converting $Z^{13}$ and $Z^{23}$ by a conventional method.

The compound (4-8) may be commercially available one or may be prepared by a conventional method. The compound (4-8) may be converted into a compound of the formula (4-7) by treating with a base such as lithium diisopropylamide, lithium hexamethyldisilazide, sodium amide, etc. in a suitable solvent to give a corresponding alkali metal salt thereof, followed by reacting with ethylene oxide. The reaction is carried out at a temperature of from −120° C. to 100° C., preferably at a temperature of from −80° C. to 20° C. The solvent may be toluene, xylene, diethyl ether, tetrahydrofuran, dioxane, etc.

Among the starting compounds (IV) for Process (a), the compound of the formula (IV) wherein n is 3 and the 4-position of the pyridine ring is a propanol group may be prepared by reacting a compound of the formula (4-9) with a compound of the formula (4-10) in the presence of a base, if necessary, converting $Z^{14}$ of the resulting compound of the formula (4-11) by a conventional method, and removing a protecting group to give a compound of the formula (4-12), if necessary, followed by converting $Z^{15}$ and $Z^{25}$ by a conventional method.

The compound (4-9) and the compound (4-10) may be commercially available ones or may be prepared by a conventional method. The compound of the formula (4-11) may be prepared by treating the compound of the formula (4-9) with a base such as lithium diisopropylamide, lithium hexamethyldisilazide, sodium amide, etc. in a suitable solvent to give an alkali metal salt thereof, and further reacting with the compound of the formula (4-10). The reaction is carried out at a temperature of from −120° C. to 100° C., preferably at a temperature of from −80° C. to 20° C. The solvent may be toluene, xylene, diethyl ether, tetrahydrofuran, dioxane, etc.

Process for Preparing a Compound of the Formula (V):

The starting compound (V) for Process (b), which is the same compound as a compound of the formula (5-3), may be prepared according to the following Scheme 5. Namely, a compound of the formula (5-1) and a compound of the formula (5-2) are reacted in the presence of a triphenylphosphine and a dialkyl azodicarboxylate in a suitable solvent to give a compound of the formula (5-3).

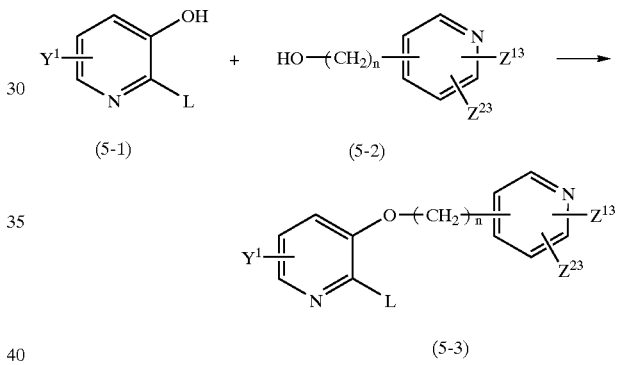

Scheme 5 wherein L, $Y^1$, $Z^{13}$, $Z^{23}$ and n are as defined above.

The compound (5-1) may be commercially available one or may be prepared by a conventional method. The dialkyl azodicarboxylate includes dimethyl azodicarboxylate, diethyl azodicarboxylate, diisopropyl azodicarboxylate, dibenzyl azodicarboxylate, etc. A trialkylphosphine such as tri-n-butylphosphine, etc., may be used instead of a triphenylphosphine. The reaction is carried out at a temperature of from −50° C. to 120° C., preferably at a temperature of from 0° C. to 80° C. The solvent may be tetrahydrofuran, toluene, xylene, dichloromethane, etc.

The compound (5-2) may be commercially available one or may be prepared according to the reaction scheme as shown in Scheme 4, in a similar manner as the preparation of the compound of the formula (4-3), the compound (4-7) and the compound (4-12) as mentioned above.

Process for Preparing a Compound of the Formula (VI):

The starting compound (VI) for Process (b) may be commercially available one or may be prepared by a conventional method.

PHARMACOLOGICAL EXPERIMENTS

The pharmacological experiments were done on the representative compounds of the present compounds. The results and the pharmacological activities of the present compounds are explained as follows.

Experiment 1

PDE IV Inhibitory Activity Test

The PDE IV inhibitory activity test was carried out according to a method using eosinophils prepared from the abdomen of guinea pig (Souness, J. E. et al., Biochem. Pharmacol. vol. 42, p. 937 (1991)). That is, a homogenizing buffer (10 ml, components: 20 mM Tris-HCl buffer (pH 7.5); 2 mM magnesium chloride; 1 mM dithiothreitol, 5 mM ethylenediamine tetraacetate disodium; 250 mM sucrose; 20 $\mu$M p-tosyl-1-lysine-chloromethylketone; 10 $\mu$g/ml Leupeptine) was added to $5 \times 10^7$ cells, and the mixture was centrifuged. To the residue was added a solubilizing buffer (10 ml, sodium deoxycholate (final concentration: 0.5%) and sodium chloride (final concentration: 100 mM) were added to the above homogenizing buffer), and the mixture was centrifuged again. The supernatant was subjected to ultrafiltration using Molcut-II (manufactured by Japan Millipore Limited), and the fraction on the membrane was collected by adding a homogenizing buffer (10 ml) to give an enzyme preparation. Inhibitory activity against the enzyme was determined by comparing the hydrolysis rates of a substrate, cAMP (manufactured by Nacalai Tesque Inc.), by the above enzyme fraction between in the test compound-treated group and the vehicle group. In addition, a 50% inhibitory concentration, i.e., $IC_{50}$, was obtained from a concentration-activity curve of a test compound. The compounds of Examples of the present invention as listed in Table 2 were used as a test compound, and Rolipram, RP-73401 and SB-207499, which are known to exhibit a PDE IV inhibitory activity, were used as a control compound. The results are shown in Table 2.

TABLE 2

PDE IV Inhibitory Activity

| Example No. | 50% Inhibitory Concentration (nM) |
|---|---|
| 3 | 35.6 |
| 7 | 33.7 |
| 14 | 15.3 |
| 15 | 9.7 |
| 30 | 11 |
| 31 | 15.7 |
| 32 | 14.2 |
| 35 | 25.8 |
| 37 | 26.8 |
| 39 | 20.5 |
| 40 | 18.3 |
| 41 | 38.6 |
| 44 | 34.6 |
| 53 | 23.4 |
| 54 | 63.3 |
| 56 | 5.6 |
| 57 | 22.9 |
| 65 | 85.6 |
| 69 | 41.2 |
| 70 | 150 |
| 73 | 200 |
| Rolipram | 28.4 |
| RP-73401 | 0.18 |
| SB-207499 | 11 |

As is clear from Table 2, the present compounds of the formula (I) exhibit a potent inhibitory activity against PDE IV isolated and purified from guinea pig eosinophils.

Experiment 2

Inhibitory Effect on Antigen-Induced Bronchoconstriction

Hartley male guinea pigs were actively sensitized by intraperitoneally administering an ovalbumin (manufacture by Sigma). Four weeks thereafter, the animals were anesthetized with Nembutal (50 mg/kg, i.p., manufactured by Dainabot Co., Ltd.), and a cannual was inserted at the airway, and the bronchoconstriction response of the animals under artificial respiration was observed. The response of the airway was measured by Konzett-Roessler method (Naunyn-Schmiedebergs, Aech. Exp. Pathol. Pharmacol., vol. 195, p. 71 (1940)). A test compound (the compounds of Examples of the present invention as listed in Table 3) was orally administered to the animals one hour prior to the administration of the antigen (i.e., ovalbumin, 0.05%/physiological saline solution, i.v.). Only the compound of Example 31 was orally administered 2 hours prior to the administration of the antigene. The inhibitory rate (%) caused by the test compound was calculated by comparing the bronchoconstriction response of the test compound-treated group with that of the control group to which only a solvent was administered. The results are shown in Table 3.

TABLE 3

Inhibitory effect on antigen-induced bronchoconstriction

| Example No. | Dose (mg/kg) | Inhibitory Rate (%) |
|---|---|---|
| 3 | 10 | 59.9 |
| 7 | 10 | 77.2 |
| 26 | 10 | 48.3 |
| 28 | 10 | 54 |
| 29 | 10 | 42 |
| 30 | 10 | 46.5 |
| 31 | 3 | 39 |
| 31 | 10 | 66 |
| 31 | 30 | 69 |
| 32 | 3 | 34 |
| 32 | 10 | 70 |
| 32 | 30 | 72 |
| 35 | 10 | 49.3 |
| 37 | 10 | 49.6 |
| 39 | 10 | 66.3 |
| 40 | 10 | 45.3 |
| 44 | 10 | 55 |
| 46 | 10 | 45.7 |
| 54 | 10 | 33 |

As is shown in Table 3, the present compounds of the formula (I) exhibited a potent inhibitory activity against the bronchoconstriction of guinea pig induced by the antigen.

As is clear from the above Pharmacological Experiments, the compounds (I) of the present invention show a potent PDE IV inhibitory activity as well as an excellent bronchodilating activity.

Besides, the present compounds (I) of the present invention are low toxic. In an acute toxicity test, for example, the compound of Example 31 never showed any toxicity even at a dose of 2000 mg/kg.

The compounds (I) of the present invention can be administered as a PDE IV inhibitor either orally, parenterally or rectally. The compounds of the present invention can also be administered by transpulmonary infiltration, oral mucous administration, trans-nasal mucous administration. The dose of the compounds of the present invention varies according to the administration routes, the conditions, ages of the patients, etc., or by the object of the administration, i.e., prophylaxis or treatment, but it is usually in the range of 0.01-100 mg/kg/day, preferably in the range of 0.1-50 mg/kg/day.

The compounds (I) of the present invention are usually administered in the form of a pharmaceutical preparation, which is prepared by mixing thereof with a pharmaceutically acceptable carrier or diluent. The pharmaceutically acceptable carrier or diluent may be any conventional ones being usually used in the pharmaceutical field, and do not react with the compounds (I) of the present invention. Suitable examples of the pharmaceutically acceptable carrier or diluent are, for example, lactose, glucose, mannitol, dextrin, starch, white sugar, magnesium metasilicate aluminate, synthetic aluminum silicate, crystalline cellulose, sodium carboxymethylcellulose, hydroxypropyl starch, calcium carboxylmethylcellulose, ion exchange resin, methylcellulose, gelatin, gum arabic, hydroxypropyl cellulose, low substituted hydroxypropyl cellulose, hydroxypropylmethylcellulose, polyvinyl-pyrrolidone, polyvinyl alcohol, light anhydrous silicic acid, magnesium stearate, talc, carboxyvinyl polymer, titanium oxide, sorbitan fatty acid ester, sodium laurylsulfate, glycerine glycerin fatty acid ester, purified lanolin, glycerogelatin, polysorbate, macrogol, vegetable oil, wax, nonionic surfactant, propyleneglycol, water, etc.

The pharmaceutical preparation is, for example, tablets, capsules, granules, powders, syrups, suspensions, suppositories, gels, injection preparations, inhalants, nasal drops, etc. These preparations may be prepared by a conventional method. In the preparation of liquids, the compound of the present invention may be dissolved or suspended in water or a suitable other solvent, when administered. Tablets and granules may be coated by a conventional method. In the injection preparations, it is preferable to dissolve the compound (I) in water, but if necessary, by using an isotonic agent, and further, a pH adjuster, a buffering agent or a preservative may be added thereto.

These preparations may contain the compound (I) of the present invention at a ratio of at least 0.01%, preferably at a ratio of 0.05–70%. These preparations may also contain other therapeutically effective compounds as well.

In addition, these preparations may be used together with an antiallergic agent, a steroid, a $\beta_2$-stimulant, an anticholinergic agent, if necessary.

BEST MODE FOR CARRYING OUT THE INVENTION

EXAMPLES

The present invention is illustrated in more detail by the following Examples, but should not be construed to be limited thereto. The identification of the compounds is carried out by Elemental analysis, hydrogen nuclear magnetic resonance spectrum ($^1$H-NMR), etc.

The following abbreviations are used in the description of $^1$H-NMR in order to simplify the description.

| | |
|---|---|
| J: | coupling constant |
| s: | singlet |
| d: | doublet |
| dd: | double doublet |
| ddd: | double double doublet |
| t: | triplet |
| dt: | double triplet |
| q: | quartet |
| m: | multiplet |

In Reference Examples and Examples, basic silica gel column chromatography was carried out using Chromatorex NH manufactured by Fuji Silysia Chemical Ltd.

Reference Example 1

Preparation of 2-(3-bromophenylthio)-3-pyridinol

2-Bromo3-pyridinol (44 g, 250 mmol) and 3-bromothiophenol (30 g, 160 mmol) are dissolved in tetrahydrofuran (hereinafter, occasionally referred to as THF) (100 ml) and dimethylformaldehyde (hereinafter, referred to as DMF) (100 ml), and the mixture is heated under reflux for 5 hours. After being allowed to cool, ethyl acetate (1000 ml) is added to the mixture, and the mixture is washed with 5% aqueous sodium hydroxide solution (50 ml×2) and a saturated brine (100 ml×2), and dried over anhydrous magnesium sulfate, and concentrated under reduced pressure. The residue is recrystallized from ethyl acetate to give the title compound (35 g) as colorless crystals, m.p. 125–126° C.

The corresponding starting compounds are reacted in a similar manner as in Reference Example 1 to give the compounds of Reference Examples 2 to 8.

Reference Example 2

2-(2-bromophenylthio)-3-pyridinol

M.p. 191–192° C.

Reference Example 3

2-(4-bromophenylthio)-3-pyridinol

M.p. 214–216° C.

Reference Example 4

2-(3-trifluoromethylphenylthio)-3-pyridinol

M.p. 125–126° C.

Reference Example 5

2-(3-fluorophenylthio)-3-pyridinol

M.p. 147–148° C.

Reference Example 6

2-(3-chlorophenylthio)-3-pyridinol

M.p. 148–149° C.

Reference Example 7

2-(3-methoxyphenylthio)-3-pyridinol

M.p. 116–117° C.

Reference Example 8

2-phenylthio3-pyridinol

M.p. 137–138° C.

Reference Example 9

Preparation of 2-(3-hydroxyphenylthio)-3-pyridinol

A mixture of 2-(3-methoxyphenylthio)-3-pyridinol (2.0 g, 8.6 mmol) obtained in Reference Example 7 and pyridine hydrochloride (17 g) is stirred at 200° C. for one hour. After being allowed to cool, the mixture is neutralized with a saturated aqueous sodium hydrogen carbonate solution, and extracted with ethyl acetate (300 ml). The organic layer is washed with a saturated brine (100 ml×2), dried over anhydrous magnesium sulfate, and concentrated to dryness under reduced pressure. The residue is purified by silica gel column chromatography (eluent: ethyl acetate), and further recrystallized from diethyl ether to give the title compound (1.24 g) as colorless crystals, m.p. 147–148° C.

Reference Example 10

Preparation of 2-bromo-3-cyclopentyloxypyridine

Triphenylphosphine (94 g, 360 mmol) and cyclopentanol (43 g, 500 mmol) are dissolved in THF (500 ml), and thereto are added with stirring diisopropyl azodicarboxylate (71 g, 350 mmol) at room temperature. To the mixture is added 2-bromo-3-pyridinol (50 g, 290 mmol) under ice-cooling, and the mixture is stirred at room temperature for 30 minutes. The reaction solution is concentrated under reduced pressure, and the residue is purified by silica gel column chromatography (eluent: ethyl acetate/hexane) to give the title compound (51 g) as a pale yellow oil.

Reference Example 11

Preparation of 2-(3-bromophenoxy)-3-pyridinol (i) 2-Bromo-3-cyclopentyloxypyridine (20 g, 83 mmol) obtained in Reference Example 10 and 3-bromophenol (26 g, 150 mmol) are dissolved in DMF (50 ml), and thereto are added potassium carbonate (42 g, 300 mmol) and cuprous bromide (18 g, 130 mmol), and the mixture is stirred at 140° C. for one hour. After being allowed to cool, the reaction solution is poured into ice, and thereto is added a 48% hydrobromic acid (50 ml), and the mixture is stirred for 15 minutes. To the mixture is added potassium carbonate (200 g), and the pH value of the mixture is adjusted to pH 12. The mixture is extracted with ethyl acetate (500 ml×2). The organic layer is washed with a saturated brine (100 ml×2), dried over anhydrous magnesium sulfate, and concentrated under reduced pressure. The residue is purified by basic silica gel column chromatography (eluent: ethyl acetate/hexane) to give 2-(3-bromophenoxy)-3-cyclopentyloxypyridine as a pale yellow oil.

(ii) The oily product obtained in the above is dissolved in acetic acid (250 ml), and thereto is added a 47% aqueous hydrobromic acid solution (100 ml), and the mixture is heated under reflux for 4 hours. The reaction solution is concentrated under reduced pressure, and neutralized with a saturated aqueous sodium hydrogen carbonate solution, and extracted with ethyl acetate (500 ml×2). The organic layer is washed with a saturated brine (100 ml×2), dried over anhydrous magnesium sulfate, and concentrated under reduced pressure. The residue is purified by basic silica gel column chromatography (eluent: ethyl acetate/hexane), and further recrystallized from isopropyl ether/hexane to give the title compound (15 g) as colorless crystals, m.p. 107–108° C.

The corresponding starting compounds are reacted in a similar manner as in Reference Example 11 to give the compounds of Reference Examples 12 to 14.

Reference Example 12

2-phenoxy-3-pyridinol

M.p. 92–93° C.

Reference Example 13

2-(3-fluorophenoxy)-3-pyridinol

M.p. 84–85° C.

Reference Example 14

2-(3-chlorophenoxy)-3-pyridinol

M.p. 86–90° C.

Reference Example 15

Preparation of 2-(3-cyanophenoxy)-3-methoxypyridine

2-Bromo-3-methoxypyridine (15 g, 68 mmol) and 3-cyanophenol (8.9 g, 75 mmol) are dissolved in DMF (150 ml), and thereto are added potassium carbonate (28 g, 0.2 mol) and cuprous bromide (10.7 g, 75 mmol), and the mixture is heated under reflux at 140° C. for 1.5 hours. After being allowed to cool, to the reaction solution is added ethyl acetate (1000 ml), and the mixture is washed with a saturated brine (200 ml×2), dried over anhydrous magnesium sulfate, and concentrated under reduced pressure. The residue is recrystallized from isopropyl ether/hexane to give the title compound (11.1 g) as pale brown crystals, m.p. 88–89° C.

Reference Example 16

Preparation of 2-(3-cyanophenoxy)-3-pyridinol 2-(3-Cyanophenoxy)-3-methoxypyridine (10 g, 44 mmol) obtained in Reference Example 15 is dissolved in methylene chloride (400 ml), and to the mixture is added a solution of boron tribromide in methylene chloride (170 ml, 170 mmol) under ice-cooling. The mixture is further stirred at room temperature for 36 hours, and the reaction is quenched by adding thereto a saturated brine. The mixture is neutralized with sodium hydrogen carbonate, and extracted with chloroform (500 ml×2). The organic layer is washed with a saturated brine (200 ml×2), dried over anhydrous magnesium sulfate, and concentrated under reduced pressure. The residue is purified by basic silica gel column chromatography (eluent: chloroform/ethanol) to give the title compound (5.2 g) as colorless crystals, m.p. 130–133° C.

Reference Example 17

Preparation of 2-(3-acetylphenoxy)-3-pyridinol 2-(3-Cyanophenoxy)-3-pyridinol (3.0 g, 14 mmol) obtained in Reference Example 16 is dissolved in THF (50 ml), and thereto is added a solution of methyl lithium in diethyl ether (21.4 ml, 30 mmol) at −70° C., and the mixture is stirred for 30 minutes. The reaction is quenched by adding thereto acetone (5 ml). The mixture is acidified with a 10% aqueous hydrochloric acid solution (15 ml), and then neutralized with saturated aqueous sodium hydrogen carbonate solution, and extracted with ethyl acetate (300 ml×2). The organic layer is washed with a saturated brine (200 ml×2), dried over anhydrous magnesium sulfate, and concentrated under reduced pressure. The residue is purified by silica gel column chromatography (eluent: ethyl acetate/hexane) to give the title compound (3.0 g) as a pale yellow oil.

Reference Example 18

Preparation of 2-(3-ethoxycarbonylphenoxy)-3-pyridinol (i) 3-Benzyloxy-2-bromopyridine (8 g, 30 mmol) and ethyl 3-hydroxybenzoate (13.3 g, 80 mmol) are dissolved in DMF (50 ml), and thereto are added potassium carbonate (28 g, 0.2 mol) and cuprous bromide (11.5 g, 80 mmol). The mixture is heated under reflux at 140° C. for one hour. After being allowed to cool, the reaction solution is acidified with a 15% aqueous hydrochloric acid solution (50 ml), and then neutralized with a saturated aqueous sodium hydrogen carbonate solution, and extracted with ethyl acetate (300 ml×2).

The organic layer is washed with a saturated brine (200 ml×2), dried over anhydrous magnesium sulfate, and concentrated under reduced pressure. The residue is purified by silica gel column chromatography (eluent: ethyl acetate/hexane) to give 3-benzyloxy-2-(3-ethoxycarbonyl-phenoxy) pyridine as a pale yellow oil.

(ii) The oily product obtained in the above is dissolved in ethanol (100 ml), and thereto is added 5% palladium carbon (1.0 g), and the mixture is stirred at room temperature for one hour under hydrogen atmosphere. The reaction solution is filtered and the insoluble materials are removed, and the filtrate is concentrated under reduced pressure. The residue is purified by basic silica gel column chromatography (eluent: ethyl acetate/ethanol), and further recrystallized from diethyl ether/hexane to give the title compound (5.4 g) as colorless crystals, m.p. 117–118° C.

Reference Example 19

Preparation of 2-(3-bromobenzolyl)-3-methoxymethoxypyridine

2-Bromo-3-methoxymethoxypyridine (22 g, 100 mmol) is dissolved in diethyl ether (500 ml), and thereto is added a solution of n-butyl lithium in hexane (69 ml, 110 mmol) under cooling at −60° C., and the mixture is stirred for 15 minutes. 3-Bromobenzaldehyde (20 g, 110 mmol) is added to the mixture, and the mixture is stirred for 10 minutes, and then the reaction is quenched with a saturated brine. The mixture is extracted with ethyl acetate (500 ml×2), and washed with a saturated brine (200 ml×2), dried over anhydrous magnesium sulfate, and concentrated under reduced pressure. The residue is dissolved in chloroform (100 ml) and hexane (300 ml), and thereto is added activated manganese dioxide (200 g). The mixture is stirred at room temperature for one hour, and the reaction solution is filtered. The filtrate is concentrated under reduced pressure, and the residue is purified by silica gel column chromatography (eluent: ethyl acetate/hexane), and further recrystallized from isopropyl ether/hexane to give the title compound (25 g) as colorless crystals, m.p. 101–102° C.

Reference Example 20

Preparation of 2-(3-bromobenzyl)-3-pyridinol 2-(3-Bromobenzolyl)-3-methoxymethoxypyridine (6.7 g, 21 mmol) obtained in Reference Example 19 is dissolved in ethylene glycol (67 ml), and thereto are added hydrazine monohydrate (3.4 ml) and potassium hydroxide (5.0 g, 76 mmol), and the mixture is stirred at 90° C. for 5 hours. After being allowed to cool, water (200 ml) is added to the mixture, and the mixture is extracted with ethyl acetate (150 ml×2), washed with a saturated brine (200 ml×2), dried over anhydrous magnesium sulfate, and concentrated under reduced pressure. The residue is recrystallized from isopropyl ether to give the title compound (4.9 g) as pale brown crystals, m.p. 160–162° C.

Reference Example 21

Preparation of 3-(3,5-dimethoxypyridin-4-yl) propenoic Acid Ethyl Ester 3,5-Dimethoxypyridine (8.1 g, 58 mmol) is dissolved in THF (100 ml), and thereto is added a solution of n-butyl lithium in hexane (45.3 ml, 70 mmol) at −20° C., and the mixture is warmed to 0° C. The mixture is stirred for 30 minutes, and cooled to −78° C. To the mixture is added DMF (5.4 ml, 70 mmol), and the mixture is warmed to 0° C. over a period of time for 30 minutes. Then, to the reaction solution is added a solution of a salt which is prepared from triethylphosphonoacetate (15.6 g, 69 mmol) and sodium hydride (60% in mineral oil, 2.78 g, 69 mmol) in THF (50 ml) at 0° C., and the mixture is stirred for one hour. The reaction solution is poured into ice-water, extracted with ethyl acetate (200 ml×2), washed with a saturated brine (100 ml×2), dried over anhydrous magnesium sulfate, and concentrated under reduced pressure. The residue is purified by silica gel column chromatography (eluent: chloroform/methanol), and further recrystallized from isopropyl ether/hexane to give the title compound (7.3 g) as colorless crystals, m.p. 100–101° C.

Reference Example 22

Preparation of 3-(3,5-dimethoxypyridin-4-yl) propionic Acid Ethyl Ester 3-(3,5-Dimethoxypyridin-4-yl)propenoic acid ethyl ester (6.5 g, 27 mmol) obtained in Reference Example 21 is dissolved in ethanol (200 ml), and thereto is added a 10% palladium carbon (1.0 g), and the mixture is stirred at room temperature under hydrogen atmosphere. After the theoretical amount of hydrogen gas is consumed, the reaction solution is filtered, and the filtrate is concentrated under reduced pressure. The residue is purified by silica gel column chromatography (eluent: ethyl acetate/hexane), and recrystallized from hexane to give the title compound (7.1 g) as colorless crystals, m.p. 66–67° C.

Reference Example 23

Preparation of 3-(3,5-dichloropyridin-4-yl)-1-propanol (i) 3,5-Dichloropyridine (4.4 g, 30 mmol) is dissolved in THF (100 ml), and thereto is added a solution of n-butyl lithium in hexane (19 ml, 30 mmol) at −70° C., and the mixture is stirred for 15 minutes. 1-Bromo-3-methoxymethoxypropane (6.0 g, 33 mmol) is added to the mixture, and the mixture is warmed to 0° C. over a period of time for one hour. The reaction is quenched with a saturated brine (50 ml), and the mixture is extracted with ethyl acetate (150 ml×2). The organic layer is washed with a saturated brine (100 ml×2), dried over anhydrous magnesium sulfate, and concentrated under reduced pressure. The residue is purified by silica gel column chromatography (eluent: ethyl acetate/hexane) to give 1-(3,5-dichloropyridin-4-yl)-3-methoxymethoxypropane (1.0 g) as an oil.

(ii) The oily product obtained in the above is dissolved in ethanol (20 ml), and thereto is added a 10% sulfuric acid (1 ml), and the mixture is heated under reflux for 30 minutes. The mixture is neutralized with a saturated aqueous sodium hydrogen carbonate solution, extracted with ethyl acetate (100 ml), washed with a saturated brine (50 ml×2), dried over anhydrous magnesium sulfate, and concentrated under reduced pressure. The residue is purified by silica gel column chromatography (eluent: ethyl acetate/hexane) to give the title compound (0.70 g) as a pale yellow oil.

Reference Example 24

Preparation of 3-(3-methoxymethoxypyridin-4-yl) propenoic Acid Ethyl Ester

3-Methoxymethoxypyridine (17.5 g, 130 mmol) is dissolved in THF (500 ml), and thereto is added a solution of n-butyl lithium in hexane (88 ml, 140 mmol) at −30° C. The mixture is stirred at 0° C. for 20 minutes, and cooled to −70° C. To the mixture is added DMF (11.0 g, 150 mmol), and the mixture is stirred again at 0° C. for 30 minutes. Then, thereto is added a solution of a salt which is prepared from triethylphosphonoacetate (34.0 g, 150 mmol) and sodium hydride (60% in mineral oil, 6.0 g, 150 mmol) in THF (200 ml) at 0° C., and the mixture is stirred for one hour. The reaction solution is poured into ice-water, extracted with ethyl acetate (400 ml×2), and the residue is purified by silica gel column chromatography (eluent: ethyl acetate/hexane) to give the title compound (22.0 g) as pale yellow oil.

Reference Example 25

Preparation of 3-(3-methoxymethoxypyridin-4-yl) propionic Acid Ethyl Ester 3-(3-Methoxymethoxypyridin-4-yl)propenoic acid ethyl ester (22.0 g, 93 mmol) obtained in Reference Example 24 is dissolved in ethanol (200 ml), and thereto is added a 5% palladium carbon (2.0 g), and the mixture is stirred at room temperature under hydrogen atmosphere. The theoretical amount of hydrogen gas is consumed, and the reaction solution is filtered, and the filtrate is concentrated under reduced pressure. The residue is purified by silica gel column chromatography (eluent: ethyl acetate/hexane) to give the title compound (21.0 g) as pale yellow oil.

Reference Example 26

Preparation of 2-bromo3-[3-(pyridine-3-yl) propoxy]pyridine 3-(Pyridin-3-yl)-1-propanol (12.3 g, 90 mmol) and triphenyl-phosphine (34.0 g, 130 mmol) are dissolved in THF (200 ml), and thereto are added successively with stirring diisopropyl azodicarboxylate (22.2 g, 110 mmol) and 2-bromo-3-hydroxypyridine (12.0 g, 69 mmol) under ice-cooling. The mixture is stirred at room temperature for 30 minutes, and then the reaction solution is concentrated under reduced pressure. To the residue is added ethyl acetate (300 ml), and the mixture is extracted with a 10% aqueous hydrochloric acid solution (150 ml×2). The pH value of the aqueous layer is adjusted with potassium carbonate to pH 12, and the mixture is extracted with ethyl acetate (200 ml×2). The organic layer is washed with a saturated brine (50 ml×2), dried over anhydrous magnesium sulfate, and concentrated under reduced pressure. The residue is purified by silica gel column chromatography (eluent: ethyl acetate/hexane) to give the title compound (18.3 g) as a colorless oil.

The corresponding starting compounds are reacted in a similar manner as in Reference Example 26 to give the compounds of Reference Examples 27 to 29.

Reference Example 27

2-bromo-3-[3-(pyridin-4-yl)propoxy]pyridine

M.p. 78–79° C.

Reference Example 28

2-chloro-3-[3-(3-methoxymethoxypyridin-4-yl)-propoxy]pyridine

Pale brown oil

Reference Example 29

2-bromo-3-[3-(3-methoxymethoxypyridin-4-yl)-propoxy]pyridine

Pale brown oil

Reference Example 30

Preparation of 3-(pyridin-3-yl)-1-butanol (i) 3-(Pyridin-3-yl)propanal (10 g, 74 mmol) is dissolved in THF (200 ml), and thereto is added a solution of trimethylsilylmethyl magnesium chloride in diethyl ether (100 ml, 100 mmol) under ice-cooling, and the mixture is stirred for 15 minutes. The reaction is quenched with a saturated brine (10 ml), and the mixture is extracted with ethyl acetate (300 ml×2), washed with a saturated brine (200 ml×2), dried over anhydrous magnesium sulfate, and concentrated under reduced pressure. To the residue are added THF (50 ml) and conc. sulfuric acid (5 ml), and the mixture is heated under reflux for 20 minutes. After being allowed to cool, the reaction solution is neutralized with a saturated aqueous sodium hydrogen carbonate solution, and extracted with ethyl acetate (200 ml×2). The organic layer is washed with a saturated brine (200 ml×2), dried over anhydrous magnesium sulfate, and concentrated under reduced pressure. The residue is purified by silica gel column chromatography (eluent: ethyl acetate/hexane) to give 3-(3-butenyl)pyridine (6.5 g) as a pale yellow oil.

(ii) The oily product obtained in the above is dissolved in THF (100 ml), and thereto is added 9-borabicyclo[3.3.1] nonane (14.0 g, 57 mmol) under ice-cooling. The ice bath is removed, and the mixture is further stirred at room temperature for 30 minutes, and thereto are carefully added again a 30% aqueous sodium hydroxide solution (30 ml), a 30% aqueous hydrogen peroxide solution (25 ml) under ice-cooling. The reaction solution is extracted with chloroform (500 ml), and the organic layer is washed with a saturated brine (200 ml×2), dried over anhydrous magnesium sulfate, and concentrated under reduced pressure. The residue is purified by silica gel column chromatography (eluent: ethyl acetate/hexane), and further subjected to Kugelrohr distillation to give the title compound (1.2 g) as a colorless oil.

Reference Example 31

Preparation of 4-(pyridin-4-yl)-1-butanol 3-(Pyridin-4-yl)propanal is treated in a similar manner as in Reference Example 30 to give the title compound as a colorless oil.

Reference Example 32

Preparation of 3-(3-bromopyridin-4-yl)-1-propanol

Diisopropylamine (7.1 g, 70 mmol) is dissolved in THF (100 ml), and thereto is added a solution of n-butyl lithium in hexane (35.7 ml, 60 mmol) at −70° C., and the mixture is stirred for 15 minutes. Then, to the mixture is added a solution of 3-bromo-4-methylpyridine (8.6 g, 50 mmol) in THF (30 ml). Ten minutes thereafter, to the mixture is added ethylene oxide (2.6 g, 60 mmol), and the mixture is warmed to 0° C. over a period of time for one hour. The reaction is quenched with a saturated brine (50 ml), and the mixture is extracted with ethyl acetate (150 ml×2). The organic layer is washed with a saturated brine (100 ml×2), dried over anhydrous magnesium sulfate, and concentrated under reduced pressure. The residue is purified by silica gel column chromatography (eluent: ethyl acetate/hexane) to give the title compound (8.5 g) as a pale yellow oil.

Reference Example 33

Preparation of 3-cyano-4-methylpyridine

3-Bromo-4-methylpyridine (20.0 g, 116 mmol) is dissolved in DMF (100 ml), and thereto is added cuprous cyanide (11.6 g, 30 mmol), and the mixture is heated under reflux for 18 hours. After cooling, a 25% aqueous ammonia (200 ml) and a saturated aqueous ammonium chloride solution (200 ml) are added to the reaction solution, and the mixture is extracted with ethyl acetate (200 ml×5). The organic layer is washed with a saturated brine (100 ml), dried over anhydrous magnesium sulfate, and concentrated under reduced pressure. The residue is purified by silica gel column chromatography (eluent: ethyl acetate/hexane) to give the title compound (11.0 g) as colorless crystals, m.p. 75–78° C.

Reference Example 34

Preparation of 3-(3-cyanopyridin-4-yl)-1-propanol

Diisopropylamine (2.5 g, 25 mmol) is dissolved in THF (30 ml), and thereto is added a solution of n-butyl lithium in hexane (14.3 ml, 24 mmol) at −70° C. The mixture is stirred for 15 minutes, and thereto is added a solution of 3-cyano-4-methylpyridine (2.4 g, 20 mmol) obtained in Reference Example 33 in THF (20 ml). Ten minutes thereafter, ethylene oxide (1.1 g, 24 mmol) is added to the mixture, and the mixture is warmed to 20° C. over a period of time for one hour. The reaction is quenched with a saturated brine (50 ml), and the mixture is extracted with ethyl acetate (150 ml×2). The organic layer is washed with a saturated brine (100 ml×2), dried over anhydrous magnesium sulfate, and concentrated under reduced pressure. The residue is purified by silica gel column chromatography (eluent: ethyl acetate/hexane) to give the title compound (1.2 g) as a pale brown oil.

Reference Example 35

Preparation of 3-(3-ethoxycarbonylpyridin-4-yl)-1-propanol

3-Cyano-4-pyridine-1-propanol (1.2 g, 7.4 mmol) obtained in Reference Example 34 is dissolved in ethanol (35 ml), and thereto is added an aqueous solution (15 ml) of sodium hydroxide (1.2 g, 30 mmol). The mixture is stirred at 45° C. for one hour, and after being allowed to cool, the mixture is neutralized with conc. hydrochloric acid (2.5 ml). The solvent is concentrated under reduced pressure, and the remaining water is removed by co-distillation with ethanol. Then, the residue is dissolved in a 30% solution of hydrochloric acid in ethanol (100 ml), and the mixture is heated under reflux for 5 hours. The reaction solution is concentrated under reduced pressure, poured into a saturated aqueous sodium hydrogen carbonate solution, and extracted with ethyl acetate (100 ml×2). The organic layer is washed with a saturated brine (50 ml×2), dried over anhydrous magnesium sulfate, and concentrated under reduced pressure. The residue is purified by silica gel column chromatography (eluent: ethyl acetate/hexane) to give the title compound (1.22 g) as a pale yellow oil.

Reference Example 36

Preparation of 3-(5-benzyloxypyridin-3-yl) propenoic Acid Ethyl Ester

Sodium hydride (60% in mineral oil, 0.71 g, 18 mmol) is suspended in THF (50 ml), and thereto is added triethylphosphono-acetate (3.5 ml, 18 mmol), and the mixture is stirred at 0° C. for 20 minutes. To the mixture is added 5-benzyloxy-3-pyridylaldehyde (2.50 g, 12 mmol), and the mixture is further stirred for 45 minutes. The reaction solution is poured into ice-water (200 ml), and the mixture is extracted with ethyl acetate (100 ml×2), washed with a saturated brine (100 ml×2), dried over anhydrous magnesium sulfate, and concentrated under reduced pressure. The residue is purified by silica gel column chromatography (eluent: ethyl acetate/hexane), and further recrystallized from isopropyl ether/hexane to give the title compound (3.1 g) as pale yellow crystals, m.p. 76–77° C.

Reference Example 37

Preparation of 1-(3,5-dichloropyridin-4-yl)-3-(tetrahydropyranyl-2-oxy)-propane

Diisopropylamine (10.1 g, 100 mmol) is dissolved in THF (200 ml), and thereto is added with stirring a solution of n-butyl lithium in hexane (57.6 ml, 95 mmol) at −70° C. Ten minutes thereafter, a solution of 3,5-dichloropyridine (13.0 g, 88 mmol) in THF (50 ml) is added dropwise to the mixture over a period of time for 15 minutes during which the bulk temperature should not be raised over −60° C., and then the mixture is further stirred for 20 minutes. Subsequently, 1-bromo-3-(tetrahydropyranyl-2-oxy) propane (20.0 g, 90 mmol) is added to the mixture, and the mixture is stirred at −70° C. for 2 hours, and cooled to 0° C. over a period of time for 5 hours. The reaction is quenched with a saturated brine (200 ml), and the mixture is extracted with ethyl acetate (300 ml×2). The extract is washed with a saturated brine (100 ml×2), dried over anhydrous magnesium sulfate, and concentrated under reduced pressure. The residue is purified by silica gel column chromatography (eluent: ethyl acetate/hexane) to give the title compound (8.6 g) as a pale yellow oil.

Reference Example 38

Preparation of 1-(3-chloro-5-methoxypyridin-4-yl)-3-(tetrahydropyranyl-2-oxy)propane 1-(3,5-Dichloropyridin-4-yl)-3-(tetrahydropyranyl-2-oxy)propane (8.0 g, 28 mmol) obtained in Reference Example 37 is dissolved in N-methylpyrrolidinone (60 ml), and thereto are added a 28% solution of sodium methylate in methanol (17.4 g, 90 mmol) and cuprous chloride (3.0 g, 30 mmol). The mixture is stirred at 110° C. for 3 hours. After being allowed to cool, to the reaction solution are added a 28% aqueous ammonia (30 ml) and water (200 ml), and the mixture is extracted with ethyl acetate (300 ml×2). The extract is washed with a saturated brine (100 ml×2), dried over anhydrous magnesium sulfate, and concentrated under reduced pressure. The residue is purified by silica gel column chromatography (eluent: ethyl acetate/hexane) to give the title compound (4.1 g) as a pale yellow oil.

Reference Example 39

Preparation of 1-(3,5-dibromopyridin-4-yl)-3-benzyloxypropane

Diisopropylamine (5.1 g, 50 mmol) is dissolved in THF (100 ml), and thereto is added with stirring a solution of n-butyl lithium in hexane (27.3 ml, 45 mmol) at −70° C. Ten minutes thereafter, a solution of 3,5-dibromopyridine (10.0 g, 42 mmol) in THF (30 ml) is added dropwise over a period of time for 20 minutes during which the bulk temperature should not be raised over −60° C., and the mixture is further stirred for 5 minutes. Subsequently, 1-bromo-3-benzyloxypropane (10.0 g, 44 mmol) is added to the mixture, and the mixture is stirred at −70° C. for 2 hours.

The mixture is warmed to 20° C. over a period of time for 2 hours. The reaction is quenched with a saturated brine (200 ml), and the mixture is extracted with ethyl acetate (300 ml×2). The extract is washed with a saturated brine (100 ml×2), dried over anhydrous magnesium sulfate, and concentrated under reduced pressure. The residue is purified by silica gel column chromatography (eluent: ethyl acetate/hexane) to give the title compound (9.0 g) as a pale yellow oil.

Reference Example 40

Preparation of 1-(3-bromo-5-methoxypyridin-4-yl)-3-benzyloxypropane 1-(3,5-Dibromopyridin-4-yl)-3-benzyloxypropane (6.0 g, 16 mmol) obtained in Reference Example 39 is dissolved in N-methyl-pyrrolidinone (40 ml), and thereto are added a 28% solution of sodium methylate in methanol (20 ml) and cuprous bromide (2.0 g, 14 mmol). The mixture is stirred at 110° C. for one hour. After being allowed to cool, to the reaction solution are added a 28% aqueous ammonia (30 ml) and water (200 ml), and the mixture is extracted with ethyl acetate (200 ml×2). The extract is washed with a saturated brine (100 ml×2), dried over anhydrous magnesium sulfate, and concentrated under reduced pressure. The residue is purified by silica gel column chromatography (eluent: ethyl acetate/hexane) to give the title compound (2.7 g) as a colorless oil.

Reference Example 41

Preparation of 1-(3-cyano-5-methoxypyridin-4-yl)-3-benzyloxypropane 1-(3-Bromo-5-methoxypyridin-4-yl)-3-benzyloxypropane (2.7 g, 8.0 mmol) obtained in Reference Example 40 is dissolved in N-methyl-pyrrolidinone (30 ml), and thereto is added cuprous cyanide (0.9 g, 10 mmol), and the mixture is stirred at 180° C. for 4 hours. After being allowed to cool, to the reaction solution are added a 28% aqueous ammonia (30 ml) and water (100 ml), and the mixture is extracted with ethyl acetate (100 ml×2). The extract is washed with a saturated brine (50 ml×2), dried over anhydrous magnesium sulfate, and concentrated under reduced pressure. The residue is purified by silica gel column chromatography (eluent: ethyl acetate/hexane) to give the title compound (2.2 g) as a pale yellow oil.

Example 1

Preparation of 3-(3,5-dimethoxypyridin-4-yl)-1-propanol

Lithium aluminum hydride (1.1 g, 30 mmol) is suspended in THF (50 ml), and thereto is added with stirring 3-(3,5-dimethoxypyridin-4-yl)propionic acid ethyl ester (3.5 g, 15 mmol) obtained in Reference Example 22 at 50° C. over a period of time for 40 minutes. The mixture is further heated under reflux for 30 minutes, and thereto are added successively water (1.1 ml), a 15% aqueous sodium hydroxide solution (1.1 ml) and water (3.3 ml) in order to quench the reaction. The reaction solution is filtered, and the insoluble materials are removed, and the filtrate is concentrated under reduced pressure. The residue is purified by silica gel column chromatography (eluent: chloroform/methanol), and further recrystallized from isopropyl ether/hexane to give the title compound (2.9 g) as colorless crystals, m.p. 88–89° C.

Example 2

Preparation of 3-(3-methoxymethoxypyridin-4-yl)-1-propanol

Lithium aluminum hydride (6.0 g, 0.16 mmol) is suspended in THF (500 ml), and thereto is added with stirring 3-(3-methoxymethoxy-pyridin-4-yl)propionic acid ethyl ester (21 g, 89 mmol) obtained in Reference Example 25 at 50° C. over a period of time for 30 minutes. The mixture is heated under reflux for 30 minutes, and thereto are added successively water (6 ml), a 15% sodium hydroxide (6 ml) and water (18 ml) in order to quench the reaction. The reaction solution is filtered to remove the insoluble materials, and the filtrate is concentrated under reduced pressure. The residue is purified by silica gel column chromatography (eluent: ethyl acetate) to give the title compound (17.5 g) as a colorless oil.

$^1$H-NMR (300 MHz, CDCl$_3$, δ ppm): 1.83–1.93 (m, 2H), 2.75 (t, 2H, J=8 Hz), 3.51 (s, 3H), 3.67 (t, 2H, J=6 Hz), 5.25 (s, 2H), 7.10 (d, 1H, J=5 Hz), 8.21 (d, 1H, J=5 Hz), 8.40 (s, 1H)

Example 3

Preparation of 2-(3-bromophenylthio)-3-[3-(pyridin-3-yl)propoxy]-pyridine 3-(Pyridin-3-yl)-1-propanol (5.5 g, 40 mmol) and triphenyl-phosphine (10.5 g, 40 mmol) are dissolved in THF (120 ml), and thereto are added successively with stirring diisopropyl azodicarboxylate (6.1 g, 30 mmol) and 2-(3-bromophenylthio)-3-pyridinol (5.0 g, 18 mmol) obtained in Reference Example 1 under ice-cooling. The mixture is further stirred at room temperature for 30 minutes, and the reaction solution is concentrated under reduced pressure. To the residue is added ethyl acetate (300 ml), and the mixture is extracted with a 10% aqueous hydrochloric acid solution (150 ml×2). The pH value of the aqueous layer is adjusted to pH 12 with potassium carbonate, and the mixture is extracted with ethyl acetate (200 ml×2). The organic layer is washed with a saturated brine (50 ml×2), dried over anhydrous magnesium sulfate, and concentrated under reduced pressure. The residue is purified by silica gel column chromatography (eluent: ethyl acetate/hexane), and recrystallized from diethyl ether to give the title compound (6.8 g) as colorless crystals, m.p. 75–76° C.

$^1$H-NMR (200 MHz, CDCl$_3$, δ ppm): 2.08–2.22 (m, 2H), 2.86 (t, 2H, J=11 Hz), 4.02 (t, 2H, J=8 Hz), 6.98–7.08 (m, 2H), 7.19–7.29 (m, 2H), 7.45 (dd, 1H, J=1 Hz, 3 Hz), 7.49 (dd, 1H, J=1 Hz, 3 Hz), 7.51–7.58 (m, 1H), 7.69 (t, 1H, J=3 Hz), 8.01 (dd, 1H, J=3 Hz, 6 Hz), 8.47 (dd, 1H, J=3 Hz, 7 Hz), 8.50 (dd, 1H, J=1 Hz, 3 Hz)

Examples 4 to 17

The corresponding starting compounds are treated in a similar manner as in Example 3 to give the compounds of Examples 4 to 17 as listed in Table 4.

TABLE 4

(Structure: pyridine with O-(CH2)n-pyridyl group, S-phenyl-X¹ substituent)

| Example | n | Attaching Position | X¹ | M.p. |
|---|---|---|---|---|
| 4 | 2 | 3 | 3-Br | Oil |
| 5 | 2 | 4 | 3-Br | 96–97° C. |
| 6 | 3 | 2 | 3-Br | Oil |
| 7 | 3 | 4 | 3-Br | 89–90° C. |
| 8 | 3 | 4 | 2-Br | Oil |
| 9 | 3 | 4 | 4-Br | Oil |
| 10 | 3 | 4 | 3-CF$_3$ | Oil |
| 11 | 3 | 4 | 3-F | 80–81° C. |
| 12 | 3 | 3 | 3-F | 138–142° C. (1.5 oxalate) |
| 13 | 3 | 4 | 3-OH | 158–159° C. |
| 14 | 3 | 4 | 3-OMe | 84–85° C. |
| 15 | 3 | 4 | H | 41–43° C. |
| 16 | 4 | 3 | 3-Br | 67–68° C. |
| 17 | 4 | 4 | 3-Br | Oil |

Example 18

Preparation of 2-(3-cyclopentyloxyphenylthio)-3-[3-(pyridin-4-yl)-propoxy]pyridine Cyclopentanol (0.11 g, 1.3 mmol) and triphenylphosphine (0.47 g, 1.8 mmol) are dissolved in THF (15 ml), and thereto are successively added with stirring diisopropyl azodicarboxylate (0.26 g, 1.3 mmol) and 2-(3-hydroxyphenylthio)-3-[3-(pyridin-4-yl)propoxy]pyridine (0.30 g, 0.89 mmol) obtained in Example 13. The mixture is further stirred at room temperature for 30 minutes, and the reaction solution is concentrated under reduced pressure. The residue is extracted with a 10% aqueous hydrochloric acid solution (30 ml), and the aqueous layer is washed with chloroform (30 ml×2), and the pH value thereof is adjusted to pH 12 with potassium carbonate. The mixture is extracted with ethyl acetate (50 ml×2), and the organic layer is washed with a saturated brine (50 ml×2), dried over anhydrous magnesium sulfate, and concentrated under reduced pressure. The residue is purified by silica gel column chromatography (eluent: chloroform/methanol) to give the title compound (0.26 g) as a colorless oil.

$^1$H-NMR (200 MHz, CDCl$_3$, δ ppm): 1.52–1.93 (m, 8H), 2.08–2.22 (m, 2H), 2.85 (t, 2H, J=8 Hz), 4.01 (t, 2H, J=6 Hz), 4.68–4.79 (m, 1H), 6.82–6.89 (m, 1H), 6.95–7.18 (m, 4H), 7.13–7.18 (m, 2H), 7.26–7.31 (m, 1H), 8.02 (dd, 1H, J=2 Hz, 4 Hz), 8.48–8.53 (m, 2H)

Example 19

Preparation of 2-(3-bromophenoxy)-3-[3-(3,5-dimethoxypyridin-4-yl)-propoxy]pyridine.difumarate 3-(3,5-Dimethoxypyridin-4-yl)-1-propanol (0.60 g, 3.0 mmol) obtained in Example 1 and triphenylphosphine (1.18 g, 4.5 mmol) are dissolved in THF (30 ml), and thereto are successively added with stirring diisopropyl azodicarboxylate (0.78 g, 3.9 mmol) and 2-(3-bromophenoxy)-3-pyridinol (1.04 g, 3.9 mmol) obtained in Reference Example 11 under ice-cooling. The mixture is stirred at room temperature for 30 minutes, and the reaction solution is concentrated under reduced pressure. To the residue is added ethyl acetate (50 ml), and the mixture is extracted with a 10% aqueous hydrochloric acid solution (50 ml×2). The pH value of the aqueous layer is adjusted to pH 12 with potassium carbonate, and the mixture is extracted with ethyl acetate (100 ml×2). The organic layer is washed with a saturated brine (50 ml×2), dried over anhydrous magnesium sulfate, and concentrated under reduced pressure. The residue is purified by silica gel column chromatography (eluent: chloroform/methanol) to give 2-(3-bromophenoxy)-3-[3-(3,5-dimethoxypyridin-4-yl) propoxy]pyridine, which is further treated with fumaric acid to give the title compound (1.26 g), m.p. 106–154° C.

Example 20

Preparation of 2-(3-bromobenzyl)-3-[3-(3,5-dimethoxypyridin-4-yl)-propoxy]pyridine.1.2 oxalate 2-(3-Bromobenzyl)-3-pyridinol obtained in Reference Example 20 and 3-(3,5-dimethoxypyridin-4-yl)-1-propanol obtained in Example 1 are treated in a similar manner as in Example 19 to give 2-(3-bromo-benzyl)-3-[3-(3,5-dimethoxypyridin-4-yl)propoxy]pyridine, which is further treated with oxalic acid to give the title compound (1.27 g), m.p. 153–165° C. (recrystallized from ethanol).

Example 21

Preparation of 2-phenoxy-3-[3-(3,5-dichloropyridin-4-yl)propoxy]-pyridine

2-Phenoxy-3-pyridinol obtained in Reference Example 12 and 3-(3,5-dichloropyridin-4-yl)-1-propanol obtained in Reference Example 23 are treated in a similar manner as in Example 19 to give the title compound as a colorless oil.

$^1$H-NMR (200 MHz, CDCl$_3$, δ ppm): 2.05–2.21 (m, 2H), 3.11 (t, 2H, J=7 Hz), 4.15 (t, 2H, J=7 Hz), 6.97 (dd, 1H, J=5 Hz, 8 Hz), 7.07–7.27 (m, 4H), 7.33–7.43 (m, 2H) 7.77 (dd, 1H, J=2 Hz, 5 Hz), 8.41 (s, 2H)

Example 22

Preparation of 2-(3-chlorophenoxy)-3-[3-(3-cyanopyridin-4-yl)propoxy]-pyridine 2-(3-Chlorophenoxy)-3-pyridinol obtained in Reference Example 14 and 3-(3-cyanopyridin-4-yl)-1-propanol obtained in Reference Example 34 are treated in a similar manner as in Example 19 to give the title compound, m.p. 146–150° C.

Example 23

Preparation of 2-(3-chlorophenoxy)-3-[3-(3-ethoxycarbonylpyridin-4-yl)-propoxy]pyridine.1.3 fumarate 2-(3-Chlorophenoxy)-3-pyridinol obtained in Reference Example 14 and 3-(3-ethoxycarbonylpyridin-4-yl)-1-propanol obtained in Reference Example 35 are treated in a similar manner as in Example 19 to give 2-(3-chlorophenoxy)-3-[3-(3-ethoxycarbonylpyridin-4-yl) propoxy]-pyridine, which is further treated with fumaric acid to give the title compound, m.p. 140–164° C. (recrystallized from isopropyl ether).

Example 24

Preparation of 2-(3-chlorophenoxy)-3-[3-(3-carboxypyridin-4-yl)-propoxy]pyridine 2-(3-Chlorophenoxy)-3-[3-(3-ethoxycarbonylpyridin-4-yl)-propoxy]pyridine (1.0 g, 2.4 mmol) obtained in Example 23 is dissolved in methanol (50 ml), and thereto is added a 1M aqueous sodium hydroxide solution (3.0 ml), and the mixture is heated under reflux for 2 hours. The methanol is evaporated under reduced pressure, and the pH value of the residue is adjusted to pH 4 with a 1M aqueous hydrochloric acid solution, and the mixture is extracted with chloroform/tetrahydrofuran (1:1) (50 ml×2), dried over anhydrous magnesium sulfate, and concentrated under reduced pressure. The residue is recrystallized from ethanol/diethyl ether to give the title compound (0.9 g) as colorless crystals, m.p. 142–144° C.

Example 25

Preparation of 2-(3-chlorophenoxy)-3-[3-(3-aminopyridin-4-yl) propoxy]-pyridine 2-(3-Chlorophenoxy)-3-[3-(3-carboxypyridin-4-yl) propoxy]-pyridine (0.50 g, 1.3 mmol) obtained in Example 24 is dissolved in tert-butanol (20 ml), and thereto are added diphenylphosphoryl azide (0.42 ml, 2.0 mmol) and triethylamine (0.27 ml, 2.0 mmol), and the mixture is heated under reflux for 8 hours. The reaction is quenched with a saturated brine (50 ml), and the reaction solution is extracted with ethyl acetate (50 ml×2). The organic layer is washed with a saturated brine (30 ml×2), dried over anhydrous magnesium sulfate, and concentrated under reduced pressure. The residue is dissolved in methylene chloride (10 ml), and thereto is added trifluoroacetic acid (5 ml), and the mixture is stirred at 25° C. for 30 minutes. The reaction solution is concentrated under reduced pressure, and to the residue is added a saturated aqueous sodium hydrogen carbonate solution (50 ml), and the mixture is extracted with ethyl acetate (50 ml×2). The organic layer is washed with a saturated brine (30 ml×2), dried over anhydrous magnesium sulfate, and concentrated under reduced pressure. The residue is purified by silica gel column chromatography (eluent; chloroform/methanol), and further recrystallized from diethyl ether to give the title compound (0.23 g) as colorless crystals, m.p. 140–142° C.

Example 26

Preparation of 2-(3-bromophenylthio)-3-[3-(3-hydroxypyridin-4-yl)-propoxy]pyridine 3-(3-Methoxymethoxypyridin-4-yl)-1-propanol (1.59 g, 9.2 mmol) obtained in Example 2 and triphenylphosphine (2.78 g, 10.6 mmol) are dissolved in THF (40 ml), and thereto are successively added with stirring diisopropyl azodicarboxylate (1.85 g, 9.2 mmol) and 2-(3-bromophenylthio)-3-pyridinol (2.00 g, 7.1 mmol) obtained in Reference Example 1 under ice-cooling. The mixture is stirred at room temperature for 30 minutes, and the reaction solution is concentrated under reduced pressure. To the residue is added ethyl acetate (50 ml), and the mixture is extracted with a 10% aqueous hydrochloric acid solution (50 ml×2). The pH value of the aqueous layer is adjusted to pH 12 with potassium carbonate, and the mixture is extracted with ethyl acetate (100 ml×2). The organic layer is washed with a saturated brine (50 ml×2), dried over anhydrous magnesium sulfate, and concentrated under reduced pressure. To the residue are added ethanol (200 ml) and a 15% aqueous hydrochloric acid solution (10 ml), and the mixture is heated under reflux for 30 minutes. The reaction solution is concentrated under reduced pressure, neutralized with a saturated aqueous sodium hydrogen carbonate solution, and extracted with ethyl acetate (100 ml×2). The organic layer is washed with a saturated brine (50 ml×2), dried over anhydrous magnesium sulfate, and concentrated under reduced pressure. The residue is purified by silica gel column chromatography (eluent: chloroform/ethyl acetate), and further recrystallized from diethyl ether to give the title compound (1.98 g) as colorless crystals, m.p. 169–171° C.

Example 27

Preparation of 2-(3-acetylphenoxy)-3-[3-(3-hydroxypyridin-4-yl)-propoxy]pyridine 2-(3-Acetylphenoxy)-3-pyridinol obtained in Reference Example 17 is treated in a similar manner as in Example 26 to give the title compound as colorless crystals, m.p. 101–102° C.

Example 28

Preparation of 2-(3-cyanophenoxy)-3-[3-(3-hydroxypyridin-4-yl)-propoxy]pyridine 2-(3-Cyanophenoxy)-3-pyridinol obtained in Reference Example 16 is treated in a similar manner as in Example 26 to give the title compound as colorless crystals, m.p. 84–86° C.

Example 29

Preparation of 2-(3-ethoxycarbonylphenoxy)-3-[3-(3-hydroxypyridin-4-yl)propoxy]pyridine.0.5 fumarate 2-(3-Ethoxycarbonylphenoxy)-3-pyridinol obtained in Reference Example 18 is treated in a similar manner as in Example 26 to give the title compound as colorless crystals, m.p. 76–79° C.

Example 30

Preparation of 2-phenoxy-3-[3-(3-hydroxypyridin-4-yl)propoxy]pyridine

2-Phenoxy-3-pyridinol obtained in Reference Example 12 is treated in a similar manner as in Example 26 to give the title compound as colorless crystals, m.p. 163–165° C.

Example 31

Preparation of 2-(3-chlorophenoxy)-3-[3-(3-hydroxypyridin-4-yl)-propoxy]pyridine 3-(3-Methoxymethoxypyridin-4-yl)-1-propanol (9.11 g, 52.6 mmol) obtained in Example 2 and triphenylphosphine (14.8 g, 56.5 mmol) are dissolved in THF (100 ml), and thereto are successively added with stirring diisopropyl azodicarboxylate (10.6 g, 52.6 mmol) and a solution of 2-(3-chlorophenoxy)-3-pyridinol (9.65 g, 43.5 mmol) obtained in Reference Example 14 in THF (100 ml) under ice-cooling. The mixture is further stirred at 50° C. for 30 minutes, and the reaction solution is concentrated under reduced pressure. To the residue is added ethyl acetate (150 ml), and the mixture is extracted with a 10% aqueous hydrochloric acid solution (150 ml×2). The pH value of the aqueous layer is adjusted to pH 12 with potassium carbonate, and the mixture is extracted with ethyl acetate (200 ml×2). The organic layer is washed with a saturated brine (50 ml×2), dried over anhydrous magnesium sulfate, and concentrated under reduced pressure. To the residue are added ethanol (500 ml) and a 15% aqueous hydrochloric acid solution (100 ml), and the mixture is heated under reflux for 30 minutes. The reaction solution is concentrated under reduced pressure, and the residue is neutralized with a saturated aqueous sodium hydrogen carbonate solution, and extracted with ethyl acetate (300 ml×2). The organic layer is washed with a saturated brine (50 ml×2), dried over anhydrous magnesium sulfate, and concentrated under reduced pressure. The residue is purified by silica gel column chromatography (eluent: hexane/ethyl acetate), and further recrystallized from diethyl ether/isopropyl ether to give the title compound (8.09 g) as colorless crystals, m.p. 109–110° C.

Example 32

Preparation of 2-(3-bromophenoxy)-3-[3-(3-hydroxypyridin-4-yl)-propoxy]pyridine 3-(3-Methoxymethoxypyridin-4-yl)-1-propanol (2.50 g, 12.7 mmol) obtained in Example 2 and triphenylphosphine (4.50 g, 17.0 mmol) are dissolved in THF (40 ml), and thereto are successively added with stirring diisopropyl azodicarboxylate (3.00 g, 15.0 mmol) and 2-(3-bromophenoxy)-3-pyridinol (2.50 g, 9.4 mmol) obtained in Reference Example 11 under ice-cooling. The mixture is further stirred at 40° C. for 30 minutes, and the reaction solution is concentrated under reduced pressure. To the residue is added ethyl acetate (50 ml), and the mixture is extracted with a 10% aqueous hydrochloric acid solution (50 ml×2). The pH value of the aqueous layer is adjusted to pH 12 with potassium carbonate, and the mixture is extracted with ethyl acetate (100 ml×2). The organic layer is washed with a saturated brine (50 ml×2), dried over anhydrous magnesium sulfate, and concentrated under reduced pressure. To the residue are added ethanol (200 ml) and a 47% aqueous hydrobromic acid solution (20 ml), and the mixture is heated under reflux for 30 minutes. The reaction solution is concentrated under reduced pressure, and neutralized with a saturated aqueous sodium hydrogen carbonate solution, and extracted with ethyl acetate (100 ml×2). The organic layer is washed with a saturated brine (50 ml×2), dried over anhydrous magnesium sulfate, and concentrated under reduced pressure. The residue is purified by silica gel column chromatography (eluent: hexane/ethyl acetate/ethanol), recrystallized from ethanol/diethyl ether to give the title compound (3.10 g) as colorless crystals, m.p. 116–118° C.

Example 33

Preparation of 2-(3-bromophenoxy)-3-[3-(3-methoxypyridin-4-yl)-propoxy]pyridine

Sodium hydride (60% in mineral oil, 0.26 g, 6.5 mmol) is suspended in DMF (30 ml), and thereto is added 2-(3-bromophenoxy)-3-[3-(3-hydroxypyridin-4-yl)propoxy] pyridine (2.0 g, 5.0 mmol) obtained in Example 32 at room temperature, and the mixture is stirred for 30 minutes. To the mixture is added methyl iodide (0.78 g, 0.34 mmol) under ice-cooling, and the mixture is further stirred for 30 minutes. To the reaction solution is added ethyl acetate (250 ml), and the organic layer is washed with a saturated brine (50 ml×2), dried over anhydrous magnesium sulfate, and concentrated under reduced pressure. The residue is purified by basic silica gel column chromatography (eluent: chloroform/ethyl acetate), and recrystallized from diethyl ether to give the title compound (0.75 g) as colorless crystals, m.p. 134–136° C.

Example 34

Preparation of 2-(3-tetrazolylphenoxy)-3-[3-(3-hydroxypyridin-4-yl)-propoxy]pyridine 2-(3-Cyanophenoxy)-3-[3-(3-hydroxypyridin-4-yl) propoxy]-pyridine (0.85 g, 2.5 mmol) obtained in Example 28 is dissolved in DMF (10 ml), and thereto are added sodium azide (0.20 g, 3.0 mmol) and ammonium chloride (0.16 g, 3.0 mmol). The mixture is stirred at 130° C. for one hour, and the reaction solution is concentrated under reduced pressure. The residue thus obtained is purified by silica gel column chromatography (eluent: acetic acid/ethanol), and recrystallized from ethanol to give the title compound (0.31 g) as pale brown crystals, m.p. 220–240° C. (decomposed).

Example 35

Preparation of 2-(3-bromophenoxy)-3-[3-(pyridin-4-yl)propoxy]pyridine

2-Bromo-3-[3-(pyridin-4-yl)propoxy]pyridine (1.0 g, 3.4 mmol) obtained in Reference Example 27 and 3-bromophenol (0.87 g, 5.0 mmol) are dissolved in DMF (10 ml), and thereto are added potassium carbonate (1.4 g, 10 mol) and cuprous bromide (0.72 g, 5.0 mmol). The mixture is heated under reflux at 140° C. for 1.5 hours. After being allowed to cool, to the reaction solution is added ethyl acetate (100 ml), and the organic layer is washed with a saturated brine (50 ml×2), dried over anhydrous magnesium sulfate, and concentrated under reduced pressure. The residue is purified by silica gel column chromatography (eluent: ethyl acetate/hexane), and recrystallized from diethyl ether to give the title compound (0.80 g) as colorless crystals, m.p. 111–113° C.

Examples 36 to 42

The corresponding starting compounds are treated in a similar manner as in Example 35 to give the compounds of Examples 36 to 42 as listed in Table 5.

TABLE 5

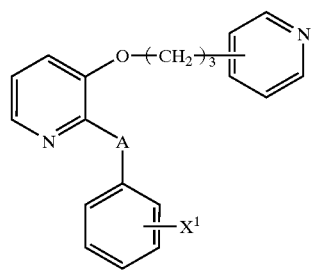

| Example | A | Attaching Position | $X^1$ | M.p. |
| --- | --- | --- | --- | --- |
| 36 | NH | 4 | 3-Br | 111–113° C. |
| 37 | O | 4 | H | 97–98° C. |
| 38 | O | 4 | 3-$CF_3$ | 62–63° C. |
| 39 | O | 4 | 3-F | 117–118° C. |
| 40 | O | 3 | 3-Br | 46–48° C. |

TABLE 5-continued

[Chemical structure: pyridine with O-(CH2)3-pyridine substituent, labeled A connecting to phenyl with X¹]

| Example | A | Attaching Position | X¹ | M.p. |
|---|---|---|---|---|
| 41 | O | 4 | 3-CN | 112–113° C. |
| 42 | O | 3 | H | 119–131° C (dihydrochloride) |

Example 43

Preparation of 2-(3,5-dichlorophenoxy)-3-[3-(3-hydroxypyridin-4-yl)-propoxy]pyridine 2-Bromo-3-[3-(3-methoxymethoxypyridin-4-yl)propoxy]pyridine (2.0 g, 5.7 mmol) obtained in Reference Example 29 and 3,5-dichloro-phenol 1.84 g, 11.3 mmol) are dissolved in DMF (10 ml), and thereto potassium carbonate (1.4 g, 10 mol) and cuprous bromide (0.86 g, 6.0 mmol), and the mixture is heated under reflux at 140° C. for 1.5 hours. After being allowed to cool, to the reaction solution is added ethyl acetate (200 ml), and the organic layer is washed with a saturated brine (50 ml×2), dried over anhydrous magnesium sulfate, and concentrated under reduced pressure. To the residue are added ethanol (200 ml) and a 15% aqueous hydrochloric acid solution (20 ml), and the mixture is heated under reflux for 30 minutes. The reaction solution is concentrated under reduced pressure, and neutralized with a saturated aqueous sodium hydrogen carbonate solution, and extracted with ethyl acetate (150 ml×2). The organic layer is washed with a saturated brine (50 ml×2), dried over anhydrous magnesium sulfate, and concentrated under reduced pressure. The residue is purified by silica gel column chromatography (eluent: chloroform/methanol), and recrystallized from diethyl ether to give the title compound (1.19 g) as colorless crystals, m.p. 99–101° C.

Example 44

Preparation of 2-(3-fluorophenoxy)-3-[3-(3-hydroxypyridin-4-yl)-propoxy]pyridine 2-Chloro-3-[3-(3-methoxymethoxypyridin-4-yl)propoxy]pyridine obtained in Reference Example 28 and 3-fluorophenol are treated in a similar manner as in Example 43 to give the title compound as colorless crystals, m.p. 68–70° C.

Example 45

Preparation of 2-(3,5-dimethoxyphenoxy)-3-[3-(3-hydroxypyridin-4-yl)-propoxy]pyridine 2-Bromo-3-[3-(3-methoxymethoxypyridin-4-yl)propoxy]pyridine obtained in Reference Example 29 and 3,5-dimethoxyphenol are treated in a similar manner as in Example 43 to give the title compound as colorless crystals, m.p. 172–178° C.

Example 46

Preparation of 2-(3-bromoanilino)-3-[3-(3-hydroxypyridin-4-yl)propoxy]-pyridine

2-Bromo-3-[3-(3-methoxymethoxypyridin-4-yl)propoxy]pyridine obtained in Reference Example 29 and 3-bromoaniline are treated in a similar manner as in Example 43 to give the title compound as pale brown crystals, m.p. 138–141° C.

Example 47

Preparation of 2-phenoxy-3-[3-(3-methoxyethoxypyridin-4-yl)propoxy]-pyridine monofumarate 2-Methoxyethanol (0.08 g, 0.93 mmol) and triphenylphosphine (0.32 g, 1.2 mmol) are dissolved in THF (20 ml), and thereto are successively added with stirring diisopropyl azodicarboxylate (0.17 g, 0.93 mmol) and 2-phenoxy-3-[3-(3-hydroxypyridin-4-yl)propoxy]pyridine (0.20 g, 0.62 mmol) obtained in Example 30 under ice-cooling. The mixture is further stirred at 60° C. for one hour, and the reaction solution is concentrated under reduced pressure. To the residue is added ethyl acetate (50 ml), and the mixture is extracted with a 10% aqueous hydrochloric acid solution (50 ml×2). The pH value of the aqueous layer is adjusted to pH 12 with potassium carbonate, and the mixture is extracted with ethyl acetate (50 ml×2). The organic layer is washed with a saturated brine (50 ml×2), dried over anhydrous magnesium sulfate, and concentrated under reduced pressure. The residue is purified by silica gel column chromatography (eluent: ethyl acetate/methanol) to give 2-phenoxy-3-[3-(3-methoxyethoxypyridin-4-yl)propoxy]pyridine, which is further treated with fumaric acid to give the title compound (0.12 g), m.p. 120–123° C. (recrystallized from diethyl ether).

Example 48

Preparation of 2-phenoxy-3-[3-(3-(2-hydroxyethoxy) pyridin-4-yl)-propoxy] pyridine.monofumarate Sodium hydride (60% in mineral oil, 0.08 g, 2.0 mmol) is suspended in DMF (5 ml), and thereto is added 2-phenoxy-3-[3-(3-hydroxypyridin-4-yl)propoxy]pyridine (0.20 g, 0.62 mmol) obtained in Example 30 at room temperature, and the mixture is stirred for 30 minutes. To the mixture is added 2-methoxymethoxyethyl bromide (0.32 g, 2.0 mmol) under ice-cooling, and the mixture is stirred at 50° C. for 30 minutes. To the reaction solution is added chloroform (100 ml), and the mixture is washed with a saturated brine (50 ml×2), dried over anhydrous magnesium sulfate, and concentrated under reduced pressure. To the residue are added ethanol (20 ml) and a 35% aqueous hydrochloric acid solution (2 ml), and the mixture is stirred at 60° C. for 30 minutes. The pH value of the reaction solution is adjusted to pH 10 with a saturated aqueous sodium hydrogen carbonate solution, and the mixture is extracted with chloroform (50 ml×2), washed with a saturated brine (50 ml×2), dried over anhydrous magnesium sulfate, and concentrated under reduced pressure. The residue is purified by silica gel column chromatography (eluent: chloroform/methanol) to give 2-phenoxy-3-[3-(3-(2-hydroxyethoxy)pyridin-4-yl)propoxy]pyridine, which is further treated with fumaric acid to give the title compound (0.17 g), m.p. 129–132° C. (recrystallized from ethanol/isopropyl ether).

Example 49

Preparation of 2-phenoxy-3-[3-(3-ethoxycarbonylmethoxy)pyridin-4-yl)-propoxy]pyridine.difumarate Sodium hydride (60% in mineral oil, 0.13 g, 3.1 mmol) is suspended in DMF (20 ml), and thereto is added 2-phenoxy-3-[3-(3-hydroxypyridin-4-yl)propoxy]pyridine (0.50 g, 1.6 mmol) obtained in Example 30 at room temperature, and the mixture is stirred for 30 minutes. To the mixture is added ethyl bromoacetate (0.34 ml, 3.1 mmol) under ice-cooling, and the mixture is stirred at room temperature for 20 minutes. To the reaction solution is added ethyl acetate (100 ml), and the mixture is washed with a saturated brine (50 ml×2), dried over anhydrous magnesium sulfate, and concentrated under reduced pressure. The residue is purified by silica gel column chromatography (eluent: ethyl acetate/hexane) to give 2-phenoxy-3-[3-(3-ethoxycarbonyl-methoxy)pyridin-4-yl)propoxy]pyridine, which is further treated with fumaric acid to give the title compound (0.22 g), m.p. 130–140° C. (recrystallized from ethanol/diethyl ether).

Example 50

Preparation of 2-phenoxy-3-[3-(3-carboxymethoxy)pyridin-4-yl)propoxy]-pyridine monofumarate 2-Phenoxy-3-[3-(3-ethoxycarbonylmethoxy)pyridin-4-yl)-propoxy]pyridine (0.30 g, 0.74 mmol) obtained in Example 49 is dissolved in ethanol (10 ml), and thereto is added a 1M aqueous sodium hydroxide solution (3 ml), and the mixture is heated under reflux for 30 minutes. The reaction solution is concentrated under reduced pressure, and thereto is added acetic acid (3 ml), and the mixture is extracted with ethyl acetate (50 ml). The organic layer is washed with a saturated brine (20 ml×1), dried over anhydrous magnesium sulfate, and concentrated under reduced pressure. The residue is purified by silica gel column chromatography (eluent: chloroform/methanol) to give 2-phenoxy-3-[3-(3-carboxymethoxy)pyridin-4-yl)propoxy]pyridine, which is further treated with fumaric acid to give the title compound (0.17 g), m.p. 167–174° C. (recrystallized from ethanol/water).

Example 51

Preparation of 2-phenoxy-3-[3-(3-methoxypyridin-4-yl)propoxy]pyridine

Sodium hydride (60% in mineral oil, 0.04 g, 1.0 mmol) is suspended in DMF (10 ml), and thereto is added 2-phenoxy-3-[3-(3-hydroxypyridin-4-yl)propoxy]pyridine (0.20 g, 0.62 mmol) obtained in Example 30 at room temperature, and the mixture is stirred for 30 minutes. To the mixture is added methyl iodide (0.06 ml, 1.0 mmol) under ice-cooling, and the mixture is stirred for 10 minutes. To the reaction solution is added ethyl acetate (50 ml), and the mixture is washed with a saturated brine (30 ml×2), dried over anhydrous magnesium sulfate, and concentrated under reduced pressure. The residue is purified by silica gel column chromatography (eluent: chloroform/methanol), and recrystallized from isopropyl ether to give the title compound (0.09 g) as colorless crystals, m.p. 101–102° C.

Example 52

Preparation of 2-(3-carboxyphenoxy)-3-[3-(pyridin-4-yl)propoxy]pyridine 2-(3-Cyanophenoxy)-3-[3-(pyridin-4-yl)propoxy]pyridine (1.15 g, 3.5 mmol) obtained in Example 41 is dissolved in methanol (50 ml), and thereto is added a 30% aqueous sodium hydroxide solution (30 ml), and the mixture is heated under reflux for 20 hours. The reaction solution is concentrated under reduced pressure, and the pH value of the mixture is adjusted to pH 3 with a 15% aqueous hydrochloric acid solution, and the mixture is extracted with chloroform/THF (2:1) (50 ml×3). The organic layer is dried over anhydrous magnesium sulfate, and concentrated under reduced pressure. The residue is purified by silica gel column chromatography (eluent: chloroform/methanol), and crystallized from diethyl ether to give the title compound (0.86 g) as colorless crystals, m.p. 208–209° C.

Example 53

Preparation of 2-(3-methoxycarbonylphenoxy)-3-[3-(pyridin-4-yl)-propoxy]pyridine 2-(3-Carboxyphenoxy)-3-[3-(pyridin-4-yl)propoxy]pyridine (0.20 g, 0.57 mmol) obtained in Example 52 is dissolved in methylene chloride (10 ml), and thereto are added 1-ethyl-3-(3'-dimethyl aminopropyl)-carbodiimide hydrochloride (0.13 g, 0.68 mmol) and methanol (0.10 ml), and the mixture is stirred at room temperature for 2 hours. To the reaction solution is added ethyl acetate (100 ml), and the mixture is washed with a saturated brine (30 ml×2), dried over anhydrous magnesium sulfate, and concentrated under reduced pressure. The residue is purified by silica gel column chromatography (eluent: chloroform/methanol) to give the title compound (0.17 g) as colorless oil.

$^1$H-NMR (200 MHz, CDCl$_3$, δ ppm): 2.07–2.24 (m, 2H), 2.59 (t, 2H, J=8 Hz), 3.89 (s, 3H), 4.06 (t, 2H, J=6 Hz), 6.99 (dd, 1H, J=5 Hz, 8 Hz), 7.10–7.14 (m, 2H), 7.20 (dd, 1H, J=2 Hz, 8 Hz), 7.35 (ddd, 1H, J=1 Hz, 2 Hz, 8 Hz), 7.47 (t, 1H, J=8 Hz), 7.76 (dd, 1H, J=2 Hz, 5 Hz), 7.77–7.80 (m, 1H, J=2 Hz), 7.86 (dt, 1H, J=1 Hz, 8 Hz), 8.47–8.51 (m, 2H)

Example 54

Preparation of 2-(3-chlorophenoxy)-3-[3-(3-acetoxypyridin-4-yl)propoxy]-pyridine.monofumarate 2-(3-Chlorophenoxy)-3-[3-(3-hydroxypyridin-4-yl)propoxy]-pyridine (1.0 g, 2.8 mmol) obtained in Example 31 is dissolved in pyridine (3 ml), and thereto is added acetic anhydride (1.3 ml, 14 mmol), and the mixture is stirred at room temperature for 5 hours. To the reaction solution is added ethyl acetate (100 ml), and the mixture is washed with a saturated brine (30 ml×2), dried over anhydrous magnesium sulfate, and concentrated under reduced pressure. The residue is purified by silica gel column chromatography (eluent: ethyl acetate/hexane) to give 2-(3-chlorophenoxy)-3-[3-(3-acetoxypyridin-4-yl)propoxy]pyridine, which is further treated with fumaric acid to give the title compound (1.07 g), m.p. 107–126° C. (recrystallized from diethyl ether).

Example 55

Preparation of 2-(3-bromophenoxy)-3-[3-(3-acetoxypyridin-4-yl)-propoxy]pyridine.1.5 oxalate 2-(3-Bromophenoxy)-3-[3-(3-hydroxypyridin-4-yl)propoxy]-pyridine obtained in Example 32 is treated in a similar manner as in Example 54 to give the title compound, m.p. 110–112° C.

Example 56

Preparation of 2-phenoxy-3-[3-(3-acetoxypyridin-4-yl)propoxy]pyridine

2-Phenoxy-3-[3-(3-hydroxypyridin-4-yl)propoxy]pyridine obtained in Example 30 is treated in a similar manner as in Example 54 to give the title compound, m.p. 79–80° C.

Example 57

Preparation of 2-(3-bromobenzyl)-3-[3-(3-acetoxypyridin-4-yl)propoxy]-pyridine.1.5 fumarate 2-(3-Bromobenzyl)-3-pyridinol obtained in Reference Example 20 is treated in a similar manner as in Example 26 to give 2-(3-bromo-benzyl)-3-[3-(3-hydroxypyridin-4-yl)propoxy]pyridine (m.p. 138–139° C.), which is further treated in a similar manner as in Example 54 to give the title compound, m.p. 122–128° C.

Example 58

Preparation of 2-(3-bromophenoxy)-3-[3-(3-hydroxy-5-methoxypyridin-4-yl)propoxy]pyridine.0.5 fumarate: and

Example 59

Preparation of 2-(3-bromophenoxy)-3-[3-(3,5-dihydroxypyridin-4-yl)-propoxy]pyridine.0.5 fumarate A mixture of 2-(3-bromophenoxy)-3-[3-(3,5-dimethoxypyridin-4-yl)propoxy]pyridine (3.15 g, 7.1 mmol) obtained in Example 19 and pyridine hydrochloride (8.0 g) is stirred at 180° C. for 1.5 hours. After being allowed to cool, to the mixture is added a saturated aqueous sodium hydrogen carbonate solution (100 ml), and the mixture is extracted with ethyl acetate (100 ml×3). The organic layer is washed with a saturated brine (50 ml×2), dried over anhydrous magnesium sulfate, and concentrated under reduced pressure. The residue is purified by silica gel column chromatography (eluent: chloroform/methanol) to give 2-(3-bromophenoxy)-3-[3-(3-hydroxy-5-methoxy-pyridin-4-yl)propoxy]pyridine and 2-(3-bromophenoxy)-3-[3-(3,5-dihydroxypyridin-4-yl)propoxy]pyridine, which are individually treated with fumaric acid to give 2-(3-bromophenoxy)-3-[3-(3-hydroxy-5-methoxypyridin-4-yl)propoxy]pyridine.0.5 fumarate (1.00 g) [m.p. 157–161° C. (recrystallized from ethanol/diethyl ether)] and 2-(3-bromophenoxy)-3-[3-(3,5-dihydroxypyridin-4-yl)propoxy]pyridine.0.5 fumarate (1.36 g) [m.p. 184–189° C. (recrystallized from ethanol)], respectively.

Example 60

Preparation of 2-(3-acetylphenoxy)-3-[3-(pyridin-4-yl)propoxy]pyridine.0.5 fumarate 2-(3-Cyanophenoxy)-3-[3-(pyridin-4-yl)propoxy]pyridine (0.50 g, 1.5 mmol) obtained in Example 41 is dissolved in THF (10 ml), and thereto is added a solution of methyl lithium in diethyl ether (2.7 ml, 3.8 mmol) at −70° C., and the mixture is stirred for 10 minutes. The mixture is warmed to 0° C. over a period of time for 30 minutes, and the reaction is quenched with a saturated brine. The reaction solution is extracted with ethyl acetate (100 ml), and the organic layer is washed with a saturated brine (50 ml×2), dried over anhydrous magnesium sulfate, and concentrated under reduced pressure. The residue is purified by silica gel column chromatography (eluent: chloroform/methanol) to give 2-(3-acetylphenoxy)-3-[3-(pyridin-4-yl)propoxy]-pyridine, which is further treated with fumaric acid to give the title compound (0.20 g), m.p. 117–119° C. (recrystallized from ethanol/diethyl ether).

Example 61

Preparation of 2-[3-(1-hydroxyethyl)phenoxy]-3-[3-(pyridin-4-yl)-propoxy]pyridine.1.0 fumarate 2-(3-Acetylphenoxy)-3-[3-(pyridin-4-yl)propoxy]pyridine (0.20 g, 0.3 mmol) obtained in Example 60 is dissolved in methanol (10 ml), and thereto is added sodium borohydride (0.50 g, 13 mmol), and the mixture is stirred at room temperature for 10 minutes. To the reaction solution is added a saturated brine (50 ml), and the mixture is extracted with ethyl acetate (100 ml). The organic layer is washed with a saturated brine (50 ml×2), dried over anhydrous magnesium sulfate, and concentrated under reduced pressure. The residue is purified by silica gel column chromatography (eluent: chloroform/methanol) to give 2-[3-(1-hydroxyethyl)phenoxy]-3-[3-(pyridin-4-yl) propoxy] pyridine, which is further treated with fumaric acid to give the title compound (0.06 g), m.p. 93–97° C. (recrystallized from ethanol/diethyl ether).

Example 62

Preparation of 3-(3-hydroxypyridin-4-yl)-1-propanol 3-(3-Methoxymethoxypyridin-4-yl)-1-propanol (3.67 g, 18.6 mmol) obtained in Example 2 is dissolved in ethanol (100 ml), and thereto is added a 15% aqueous hydrochloric acid solution (20 ml), and the mixture is heated under reflux for 30 minutes. The reaction solution is concentrated under reduced pressure, and the residue is purified by silica gel column chromatography (eluent: hexane/ethyl acetate), and further recrystallized from diethyl ether to give the title compound (2.08 g) as colorless crystals, m.p. 123–126° C.

Example 63

Preparation of 3-[3-(2,6-dimethoxybenzolyloxy)pyridin-4-yl]-1-propanol (i) 3-(3-Hydroxypyridin-4-yl)-1-propanol (1.00 g, 6.53 mmol) obtained in Example 62 is dissolved in THF, and thereto are added dihydropyrane (5.0 ml, 55 mmol), D,L-camphore-10-sulfonic acid (1.00 g, 4.30 mmol), and the mixture is heated under reflux for 20 minutes. The reaction solution is poured into an aqueous sodium hydrogen carbonate solution, and the mixture is extracted with ethyl acetate (200 ml×2), dried over anhydrous magnesium sulfate, and concentrated under reduced pressure. The residue is purified by silica gel column chromatography (eluent: hexane/ethyl acetate) to give 3-hydroxy-4-(3-tetrahydropyranyloxypropyl)pyridine as colorless oil.

(ii) The oily product obtained in the above is dissolved in pyridine (12 ml), and thereto is added 2,6-dimethoxybenzolyl chloride (4.6 g, 7.4 mmol), and the mixture is stirred at room temperature for 10 minutes. To the reaction solution is added ethyl acetate (300 ml), and the mixture is successively washed with a saturated aqueous sodium hydrogen carbonate solution (50 ml×2), a saturated aqueous cuprous sulfate solution (50 ml×2) and a saturated brine (50 ml×2), dried over anhydrous magnesium sulfate, and concentrated under reduced pressure. The residue is purified by silica gel column chromatography (eluent: hexane/ethyl acetate) to give 3-(2,6-dimethoxybenzolyloxy)-4-(3-tetrahydropyranyloxypropyl)pyridine as a colorless oil.

(iii) The oily product obtained in (ii) is added to methanol (100 ml) and a 10% aqueous hydrochloric acid solution (5 ml), and the mixture is stirred at 40° C. for 30 minutes. After cooling, the reaction solution is neutralized with a saturated aqueous sodium hydrogen carbonate solution, extracted with ethyl acetate (400 ml), and washed with a saturated brine (50 ml×2). The mixture is dried over anhydrous magnesium sulfate, and concentrated under reduced pressure. The residue is recrystallized from diethyl ether to give the title compound (0.80 g) as colorless crystals, m.p. 117–118° C.

Example 64

Preparation of 3-(5-benzyloxypyridin-3-yl)propanol 3-(5-Benzyloxypyridin-3-yl)propenoic acid ethyl ester (2.65 g, 9.4 mmol) obtained in Reference Example 36 is dissolved in ethanol (150 ml), and thereto is added sodium borohydride (3.54 g, 94 mmol), and the mixture is heated under reflux for 3 hours. The reaction solution is evaporated under reduced pressure, and to the residue is added water (100 ml) and the mixture is extracted with ethyl acetate (100 ml×2). The extract is washed with a saturated brine (50 ml×2), dried over anhydrous magnesium sulfate, and concentrated under reduced pressure. The residue is purified by silica gel column chromatography (eluent: ethyl acetate/hexane) to give the title compound (1.8 g) as a pale yellow oil.

$^1$H-NMR (300 MHz, CDCl$_3$, δ ppm): 1.80–2.10 (m, 3H), 2.71 (t, 2H, J=8 Hz), 3.66 (t, 2H, J=6 Hz), 5.10 (s, 2H), 7.11 (t, 1H, J=2 Hz), 7.30–7.48 (m, 5H), 8.09 (d, 1H, J=2 Hz), 8.21 (d, 1H, J=2 Hz)

Example 65

Preparation of 2-(3-chlorophenoxy)-3-[3-(5-hydroxypyridin-3-yl)-propoxy]pyridine 2-(3-Chlorophenoxy)-3-pyridinol obtained in Reference Example 14 and 3-(5-benzyloxypyridin-3-yl)-1-propanol obtained in Example 64 are treated in a similar manner as in Example 3 to give 2-(3-chloro-phenoxy)-3-[3-(5-benzyloxypyridin-3-yl)propoxy]pyridine.

2-(3-Chlorophenoxy)-3-[3-(5-benzyloxypyridin-3-yl) propoxy]-pyridine (2.5 g, 5.6 mmol) thus obtained is dissolved in ethanol (100 ml), and thereto is added conc. hydrochloric acid (100 ml), and the mixture is heated under reflux. At 5 hours thereafter and at 10 hours thereafter, conc. hydrochloric acid (50 ml×2) is added to the mixture, and then the mixture is refluxed for 20 hours, and allowed to cool. The mixture is neutralized with an aqueous sodium hydrogen carbonate solution, and extracted with ethyl acetate (100 ml×2). The extract is washed with a saturated brine (50 ml×2), dried over anhydrous magnesium sulfate, and concentrated under reduced pressure. The residue is purified by silica gel column chromatography (eluent: ethyl acetate/hexane), and recrystallized from ethyl acetate/hexane to give the title compound (1.3 g) as colorless crystals, m.p. 148–149° C.

Example 66

Preparation of 3-(3-ethoxycarbonyl-5-methoxypyridin-4-yl)-1-propanol 1-(3-Cyano-5-methoxypyridin-4-yl)-3-benzyloxypropane (2.3 g, 8 mmol) obtained in Reference Example 41 is dissolved in ethanol (35 ml), and thereto is added a 10% aqueous sodium hydroxide solution (15 ml), and the mixture is stirred at 70° C. for 1.5 hours. The mixture is neutralized with conc. hydrochloric acid, and the reaction solution is concentrated under reduced pressure. The residue thus obtained is dissolved in a 30% solution of hydrochloric acid in ethanol (50 ml), and the mixture is heated under reflux for 14 hours. The mixture is neutralized with sodium hydrogen carbonate, and the reaction solution is concentrated again under reduced pressure. The resultant is extracted with ethyl acetate (200 ml), washed with a saturated brine (50 ml×2), dried over anhydrous magnesium sulfate, and concentrated under reduced pressure. The residue is purified by silica gel column chromatography (eluent: ethyl acetate/hexane), and recrystallized from ether to give the title compound (0.60 g) as colorless crystals, m.p. 85–89° C.

Example 67

Preparation of 2-(3-chlorophenoxy)-3-[3-(3-ethoxycarbonyl-5-methoxy-pyridin-4-yl)propoxy]pyridine 2-(3-Chlorophenoxy)-3-pyridinol obtained in Reference Example 14 and 3-(3-ethoxycarbonyl-5-methoxypyridin-4-yl)-1-propanol obtained in Example 66 are treated in a similar manner as in Example 3 to give the title compound, m.p. 82–83° C.

Example 68

Preparation of 2-(3-chlorophenoxy)-3-[3-(3-carboxyl-5-methoxypyridin-4-yl) propoxy]pyridine 2-(3-Chlorophenoxy)-3-[3-(3-ethoxycarbonyl-5-methoxypyridin-4-yl)propoxy]pyridine (4.4 g, 10 mmol) obtained in Example 67 is dissolved in ethanol (40 ml), and thereto is added a solution of sodium hydroxide (0.80 g, 20 mmol) in water (5 ml), and the mixture is stirred at 70° C. for 30 minutes. The mixture is concentrated under reduced pressure, and thereto is added water (50 ml), and further thereto is added dropwise acetic acid (3 ml) with stirring. The precipitated crystals are collected by filtration, washed with water, and dried to give the title compound (3.6 g) as colorless crystals, m.p. 166–168° C.

Example 69

Preparation of 2-(3-chlorophenoxy)-3-[3-(3-amino-5-hydroxypyridin-4-yl)propoxy]pyridine.1.0 fumarate 2-(3-Chlorophenoxy)-3-[3-(3-carboxyl-5-methoxypyridin-4-yl)-propoxy]pyridine (3.8 g, 9.2 mmol) obtained in Example 68 is suspended in toluene (40 ml), and thereto is added triethylamine (3.5 g, 35 mmol), and further thereto are added diphenylphosphoryl azide (4.1 g, 15 mmol) at 70° C. for 30 minutes. Then, p-methoxybenzyl alcohol (3.5 g, 25 mmol) is added to the mixture, and 30 minutes thereafter, ethyl acetate (300 ml) is added to the reaction solution. The mixture is washed with a saturated aqueous sodium hydrogen carbonate solution and a saturated brine (50 ml×2), dried over anhydrous magnesium sulfate, and concentrated under reduced pressure. The residue is purified by silica gel column chromatography (eluent: ethyl acetate/hexane) to give 2-(3-chlorophenoxy)-3-{3-[3-(4-methoxy benzyloxy-carbonyl)amino-5-hydroxypyridin-4-yl]propoxy}pyridine (3.5 g) as a pale yellow oil.

The oily product thus obtained is mixed with pyridine hydrochloride (30 g), and the mixture is stirred for melting at 150° C. for 1.5 hours. After being allowed to cool, water (100 ml) is added to the mixture, and the mixture is neutralized with sodium hydrogen carbonate, and extracted with chloroform (100 ml×4). The chloroform layers are combined, dried over anhydrous magnesium sulfate, and concentrated under reduced pressure. The residue is purified by basic silica gel column chromatography (eluent: ethanol/chloroform) to give 2-(3-chlorophenoxy)-3-[3-(3-amino-5-hydroxypyridin-4-yl)propoxyl]-pyridine (0.85 g) as a pale brown oil, which is further treated with fumaric acid to give the title compound (0.53 g), m.p. 75–90° C. (recrystallized from ethyl acetate).

Example 70

Preparation of 2-(3-chlorophenoxy)-3-[3-(3-methylsulfonylaminopyridin-4-yl)propoxy]pyridine 2-(3-Chlorophenoxy)-3-[3-(3-aminopyridin-4-yl)propoxy]pyridine (0.15 g, 0.42 mmol) obtained in Example 25 is dissolved in methylene chloride (5 ml) and pyridine (0.34 ml), and thereto is added ethylsulfonyl chloride (0.04 ml, 0.50 mmol) under ice-cooling, and the mixture is stirred for 3 hours. To the mixture is added ice-water (20 ml), and the mixture is extracted with ethyl acetate (50 ml×2). The organic layer is washed with a saturated aqueous sodium hydrogen carbonate solution (20 ml×2) and a saturated brine (20 ml×2), dried over anhydrous magnesium sulfate, and concentrated under reduced pressure. The residue is purified by basic silica gel column chromatography (eluent: chloroform/methanol), and further recrystallized from diethyl ether to give the title compound (0.07 g) as colorless crystals, m.p. 131–133° C.

Example 71

Preparation of 3-(3-chloro-5-methoxypyridin-4-yl)-1-propanol 1-(3-Chloro-5-methoxypyridin-4-yl)-3-(tetrahydropyranyl-2-oxy)propane (4.0 g, 14 mmol) obtained in Reference Example 38 is dissolved in ethanol (100 ml), and thereto is added a 15% aqueous hydrochloric acid solution (3 ml), and the mixture is stirred at 60° C. for 20 minutes. The reaction solution is concentrated under reduced pressure, and the residue thus obtained is purified by basic silica gel column chromatography (eluent: ethyl acetate) to give the title compound (2.2 g) as a pale yellow oil.

$^1$H-NMR (300 MHz, CDCl$_3$, δ ppm): 1.77 (t, 1H, J=6 Hz), 1.80–1.89 (m, 2H), 2.89 (t, 2H, J=7 Hz), 3.63 (q, 2H, J=7 Hz), 3.95 (s, 3H), 8.12 (s, 1H), 8.23 (s, 1H)

Example 72

Preparation of 2-(3-chlorophenoxy)-3-[3-(3-chloro-5-methoxypyridin-4-yl)propoxy]pyridine 2-(3-Chlorophenoxy)-3-pyridinol obtained in Reference Example 14 and 3-(3-chloro-5-methoxypyridin-4-yl)-1-propanol obtained in Example 71 is treated in a similar manner as in Example 3 to give the title compound (2.7 g) as colorless oil.

$^1$H-NMR (300 MHz, CDCl$_3$, δ ppm): 2.03–2.15 (m, 2H), 2.95 (t, 2H, J=7 Hz), 3.87 (s, 3H), 4.08 (t, 2H, J=7 Hz), 6.97–7.06 (m, 2H), 7.11–7.17 (m, 2H), 7.20 (dd, 1H, J=2 Hz, 8 Hz), 7.26–7.33 (m, 1H), 7.76 (dd, 1H, J=2 Hz, 5 Hz), 8.09 (s, 1H), 8.21 (s, 1H)

Example 73

Preparation of 2-(3-chlorophenoxy)-3-[3-(3-chloro-5-hydroxypyridin-4-yl)propoxy]pyridine 2-(3-Chlorophenoxy)-3-[3-(3-chloro-5-methoxypyridin-4-yl)-propoxy]pyridine (8.5 g, 21 mmol) obtained in Example 72 and pyridine hydrochloride (100 g, 0.86 mol) are mixed, and the mixture is stirred for melting at 150° C. for one hour. To the mixture is added ice-water (300 ml), and the mixture is neutralized with sodium hydrogen carbonate, and extracted with ethyl acetate (100 ml×3). The organic layer is washed with a saturated aqueous sodium hydrogen carbonate solution (50 ml×2) and a saturated brine (50 ml×2), dried over anhydrous magnesium sulfate, and concentrated under reduced pressure. The residue is purified by basic silica gel column chromatography (eluent: ethanol/ethyl acetate), and further recrystallized from diethyl ether/diisopropyl ether to give the title compound (5.6 g) as colorless crystals, m.p. 95–96° C.

Preparation: Production of Tablets

The following components are mixed and kneaded in a conventional manner, and the mixture is granulated. The mixture is further compressed for tabletting to give 1,000 tablets (each 100 mg).

2-(3-Chlorophenoxy)-3-[(3-hydroxypyridin-4-yl)propoxy]pyridine (the compound of Example 31) (5 g),
Corn starch (25 g),
Lactose (54 g),
Crystalline cellulose (11 g),
Hydroxypropyl cellulose (3 g),
Light anhydrous silicic acid (1 g), and
Magnesium stearate (1 g).

Industrial Applicability

The compounds (I) of the present invention show a potent PDE IV inhibitory activity as well as an excellent bronchodilating activity, and hence, they are widely useful as a PDE IV inhibitor in the treatment or prophylaxis of allergic inflammatory diseases or organ inflammatory diseases. Especially they are useful in the treatment or prophylaxis of pulmonary diseases accompanied by airway obstruction such as asthma.

What is claimed is:

1. A process for preparing a compound of the formula (I):

(I)

wherein A is an oxygen atom, a sulfur atom, or CHR$^1$ or NR$^2$, R$^1$ and R$^2$ are a hydrogen atom or a lower alkyl group; X$^1$ and X$^2$ are the same or different and each a hydrogen atom, a halogen atom, a nitro group, a cyano group, a hydroxy group, a lower alkyl group, a hydroxy-substituted lower alkyl group, a halogeno-lower alkyl group, a lower alkoxy group, a cyclo-lower alkoxy group, a hydroxy-substituted lower alkoxy group, a halogeno-lower alkoxy group, a lower alkoxy-substituted lower alkoxy group, a carboxy-substituted lower alkoxy group, a lower alkoxycarbonyl-substituted lower alkoxy group, a carboxyl group, a lower alkoxy-carbonyl group, a mono- or di-lower alkylaminocarbonyl group, a lower acyl group, a lower acyloxy group, an amino group, a lower acylamino group, a carbamoyl group, a 5-tetrazolyl group, or a group which can be converted into a hydroxy group in viuo, Y$^1$ is a hydrogen atom or a lower alkyl group, Z$^1$ and Z$^2$ are the same or different, and each a hydrogen atom, a halogen atom, a cyano group, a hydroxy group, a lower alkyl group, a hydroxy-substituted lower alkyl group, a halogeno-lower alkyl group, a lower alkoxy group, a cyclo-lower alkoxy group, a hydroxy-substituted lower alkoxy group, a halogeno-lower alkoxy group, a lower alkoxy-substituted lower alkoxy group, a carboxy-substituted lower alkoxy group, a lower alkoxycarbonyl-substituted lower alkoxy group, a carboxyl group, a lower alkoxycarbonyl group, a mono- or di-lower alkylaminocarbonyl group, a lower acyloxy group, an amino group, a mono- or di-lower alkylamino group, a lower acylamino group, a lower alkoxycarbonylamino group, a lower alkylsulfonylamino group, a carbamoyl group, a 5-tetrazolyl group, or a group which can be converted into a hydroxy group in vivo, and n is an integer of 2 to 4, or a pharmaceutically acceptable salt thereof, which comprises condensing a compound of the formula (III):

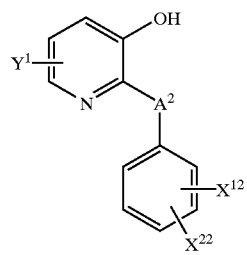

(III)

wherein $A^2$ is an oxygen atom, a sulfur atom or $CHR^1$, $X^{12}$ and $X^{22}$ are the same or different and each a hydrogen atom, a halogen atom, a nitro group, a cyano group, a lower alkyl group, a halogeno-lower alkyl group, a lower alkoxy group, a cyclo-lower alkoxy group, a halogeno-lower alkoxy group, a lower alkoxy-substituted lower alkoxy group, a lower alkoxycarbonyl group, a lower acyl group, or a lower acyloxy group, and $R^1$ and $Y^1$ are as defined above, with a compound of the formula (IV):

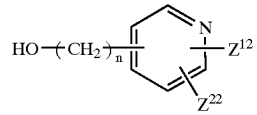

(IV)

wherein $Z^{12}$ and $Z^{22}$ are the same or different and each a hydrogen atom, a halogen atom, a cyano group, a hydroxy group, a lower alkyl group, a lower alkoxy group, a cyclo-lower alkoxy group, a lower alkoxy-substituted lower alkoxy group, a lower alkoxycarbonyl group, a lower acyloxy group, a benzyloxy group, a benzoyloxy group, a mono- or di-lower alkoxy-substituted benzoyl group, a mono- or di-lower alkoxy-substituted benzoyloxy group, an amino group, a lower alkoxycarbonyl-amino group, or a lower alkylsulfonylamiflo group, and n is as defined above.

* * * * *